(12) United States Patent
Jardine et al.

(10) Patent No.: US 11,149,034 B2
(45) Date of Patent: Oct. 19, 2021

(54) DERIVATIVES OF LUCIFERIN AND METHODS FOR THEIR SYNTHESIS

(71) Applicant: UNIVERSITY OF CAPE TOWN, Cape Town (ZA)

(72) Inventors: Moegamat Anwar Jardine, Cape Town (ZA); Marwaan Rylands, Cape Town (ZA)

(73) Assignee: UNIVERSITY OF CAPE TOWN, Cape Town (ZA)

( * ) Notice: Subject to any disclaimer, the term of this patent is extended or adjusted under 35 U.S.C. 154(b) by 0 days.

(21) Appl. No.: 16/633,859

(22) PCT Filed: Jul. 25, 2018

(86) PCT No.: PCT/IB2018/055542
§ 371 (c)(1),
(2) Date: Jan. 24, 2020

(87) PCT Pub. No.: WO2019/021202
PCT Pub. Date: Jan. 31, 2019

(65) Prior Publication Data
US 2020/0331902 A1 Oct. 22, 2020

(30) Foreign Application Priority Data
Jul. 25, 2017 (GB) ...................................... 1711983

(51) Int. Cl.
*C07D 417/04* (2006.01)
*C07D 277/68* (2006.01)
*C07D 417/12* (2006.01)
*A61K 49/00* (2006.01)

(52) U.S. Cl.
CPC ........ *C07D 417/04* (2013.01); *A61K 49/0021* (2013.01); *C07D 277/68* (2013.01); *C07D 417/12* (2013.01)

(58) Field of Classification Search
CPC ... C07D 417/04; C07D 277/68; C07D 417/12
See application file for complete search history.

(56) References Cited

FOREIGN PATENT DOCUMENTS

| EP | 1835034 A1 | 9/2007 |
|---|---|---|
| EP | 1935986 A2 | 6/2008 |
| WO | WO-2011/146390 A2 | 11/2011 |

OTHER PUBLICATIONS

Sharma et al. Org. Lett. 2017, 19, 5836-5839 (Year: 2017).*
Steinhardt et al. ChemBioChem 2017, 18, 96-100 (Year: 2017).*
Besson et al. J. Chem. Soc., Perkin Trans. 1, 1998, 3925-3926 (Year: 1998).*
Emmanuel Deau et al., "Microwave-assisted synthesis of novel N-(4-phenylthiazol-2-yl)-benzo[d]thiazole-, thiazolo[4,5-b]pyridine-, thiazolo[5,4-b]pyridine- and benzo[d]oxazole-2-carboximidamides inspired by marine topsentines and nortopsentines", *Tetrahedron*, vol. 70, No. 35, pp. 5532-5540 (2014).
Chi B. Vu et al., "Discovery of benzothiazole derivatives as efficacious and enterocyte-specific MTP inhibitors ", *Bioorganic & Medicinal Chemistry Letters*, vol. 19, No. 5, pp. 1416-1420 (2009).
Stephane Frere et al., "Novel 6-substituted benzothiazol-2-yl indolo[1,2-c] quinazolines", Tetrahedron, vol. 59, No. 6, pp. 773-779 (2003).
Thierry Besson et al., "New route to 2-cyanobenzothiazoles via N-arylimino-1 ,2,3-dithiazoles+", *J. Chem. Soc., Perkin Trans.* 1, No. 23, pp. 3925-3926 (1998).
Rachel Steinhardt et al., "Brominated Luciferins Are Versatile Bioluminescent Probes", *ChemBioChem*, vol. 18, pp. 96-100 (2016).
Deepak K. Sharma et al., "Rapid Access to a Broad Range of 6'-Substituted Firefly Luciferin Analogues Reveals Surprising Emitters and Inhibitors", *Organic Letters*, vol. 19, No. 21, pp. 5836-5839 (2017).
Thierry Besson et al., "Rapid synthesis of 2-cyanobenzothiazole, isothiocyanate and cyanoformanalide derivatives of dapsone", *J. Chem. Soc., Perkin Trans. 1*, pp. 563-566 (2000).
International Search Report and Written Opinion for Application No. PCT/IB2018/055542, dated Dec. 11, 2018.
Office Action, corresponding European Patent Application No. 18762136.2, dated Feb. 10, 2021.
Jean Claude Arnould et al., "Convenient Synthesis of Aromatic Thiols from Phenols", *Tetrahedron Letters*, vol. 37, No. 26, pp. 4523-4524 (1996).

* cited by examiner

*Primary Examiner* — Matthew P Coughlin
(74) *Attorney, Agent, or Firm* — Marshall, Gerstein & Borun LLP

(57) ABSTRACT

6-Thio derivatives of D-luciferin, also referred to as D-thioluciferins, having the general structure of Formula (I) are provided. Methods for synthesising D-luciferin, its derivatives, and their related 2-cyanobenzothiazole precursors are also provided. These compounds are commercially valuable due to their application in optical imaging, particularly in bioluminescence imaging.

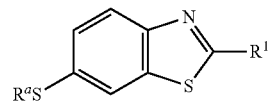

Formula (I)

14 Claims, 8 Drawing Sheets
Specification includes a Sequence Listing.

DERIVATIVES OF LUCIFERIN AND METHODS FOR THEIR SYNTHESIS

CROSS-REFERENCE TO RELATED APPLICATIONS

This application claims priority to United Kingdom patent application no. 1711983.5 which is incorporated by reference herein.

INCORPORATION BY REFERENCE OF MATERIAL SUBMITTED ELECTRONICALLY

This application contains, as a separate part of disclosure, a sequence listing in computer-readable form (filename: 55276_SeqListing.txt; 5,085 bytes; created Jan. 24, 2020 which is incorporated by reference in its entirety.

FIELD OF THE INVENTION

The invention relates to derivatives of the molecule, D-luciferin, and methods for their synthesis.

BACKGROUND TO THE INVENTION

Luciferins are light emitting compounds which are oxidised by luciferase enzymes to form short-lived high energy state intermediates that decay spontaneously to their ground state products, giving off light in the process. D-luciferin, also known as firefly luciferin, is a light emitting compound that is a substrate of the enzyme, luciferase.

Luciferase is a generic term for the class of oxidative enzymes that produce bioluminescence in combination with luminescent substrates, such as D-luciferin. Luciferases are produced by a number of different organisms including fireflies, clickbeetles, copepods, jellyfish, sea pansies, Jack-O-Lantern mushrooms, luminous fungi and dinoflagellates. Luciferases can be synthetically produced through genetic engineering and may be modified for enhanced stability or to accommodate different substrates. Luciferase genes can be synthesized and inserted into organisms or transfected into cells, such as the cells of humans, mice or rats, to image cells or tissue.

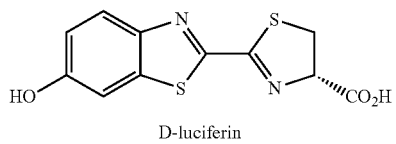 [SMILES: O=C(O)[C@H]1CSC(c2nc3ccc(O)cc3s2)=N1]
D-luciferin

D-luciferin is oxidised by luciferase to form an unstable 1,2-dioxetane intermediate in the presence of ATP, oxygen and magnesium ions. The intermediate decays to form carbon dioxide and excited carbonyl compounds, which release their excess energy in the form of light (Scheme 1).

Scheme 1. Synthesis of D-Luciferin from key intermediate, 2-cyano-6-hydroxybenzothiazole.

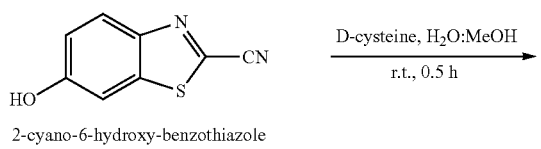
2-cyano-6-hydroxy-benzothiazole

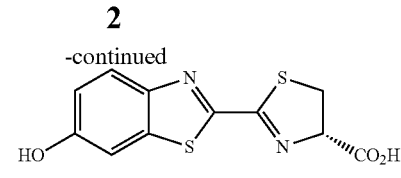
D-luciferin

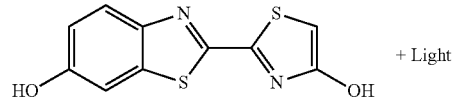
+ Light

Existing methods of producing D-luciferin typically start with construction of a 2-cyano-6-hydroxybenzothiazole intermediate, requiring over 7 synthetic steps. The addition of D-cysteine (D-cys) to the cyano moiety yields D-luciferin almost quantitatively. The total synthesis of D-luciferin has an overall yield of only 9% over 9 synthetic steps, making it costly and impractical. Moreover, preparation of certain luciferin derivatives requires the use of a palladium (II) catalyst, which is expensive to use and can be poisoned by sulphur-containing reagents. There is therefore a need for new synthetic methods of producing luciferins and their derivatives.

D-luciferin and luciferase are used extensively in bioluminescence imaging for non-invasive monitoring of biological processes, with particular application in cancer research where laboratory rodent models are used to monitor cancer in mammalian tissues. D-luciferin emits light at a relative emission of $\lambda_{max}$=594 nm (i.e. green or nearly yellow light on the visible light spectrum). Light of this frequency is well absorbed by biological tissue making is suitable for use in bioimaging. Various derivatives of D-luciferin are known, with different derivatives having application in different types of studies.

Derivatives of D-luciferin in which the 6'-hydroxyl has been converted to an amine to afford D-aminoluciferin are known. D-aminoluciferin has been used to construct biological probes having a hydrolysable amide bond. Many other derivatives have been prepared by various research groups in an effort to yield new bioluminogenic substrates that may be applied in bioimaging. In most cases, the derivatives are based on modifications of either the natural 6'-hydroxy-D-luciferin or the 6'-amino-D-luciferin. Although useful, these substrates have limited application and are unsuitable for use in certain chemical reactions.

There is therefore room for further derivatives of luciferin that can be used in bioluminescence imaging and other applications, which emit light at different frequencies and intensities to D-luciferin.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with a first aspect of this invention, there is provided a compound having the structure of Formula (I):

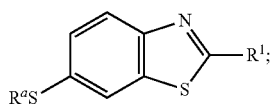

Formula (I)

wherein:
R¹ is CN or

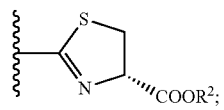

R² is H or optionally substituted alkyl;
Rᵃ is H, halogen, —SR³, optionally substituted alkyl, optionally substituted haloalkyl, optionally substituted cycloalkyl, optionally substituted heterocyclyl, acyl,

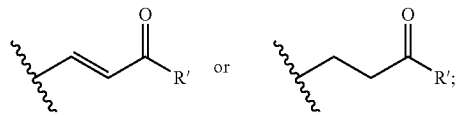

R³ is optionally substituted alkyl, optionally substituted haloalkyl, optionally substituted cycloalkyl, optionally substituted heterocyclyl, optionally substituted aryl or optionally substituted heteroaryl;
R' is H, optionally substituted alkyl, optionally substituted aryl or OR''; and
R'' is H, optionally substituted alkyl or optionally substituted aryl; or a salt, hydrate or solvate thereof.
R² may be H or optionally substituted benzyl (Bn).
and/or R³ may be

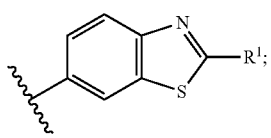

Rᵃ may be H, halogen, —SR³ or optionally substituted alkyl;
R³ may be

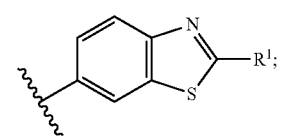

and the compound may be selected from the group consisting of:

1-1
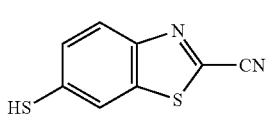

1-2
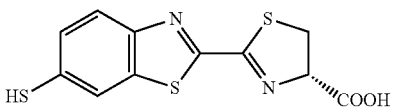 [SMILES: O=C(O)[C@H]1CSC(c2nc3ccc(S)cc3s2)=N1]

1-3
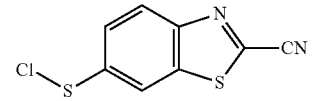

1-4
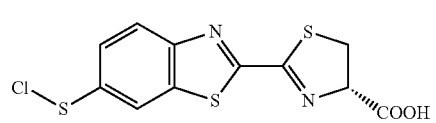

1-5
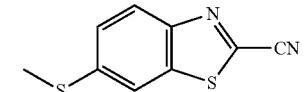

1-6
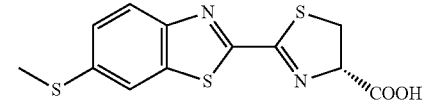

1-7
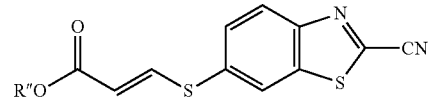

1-8
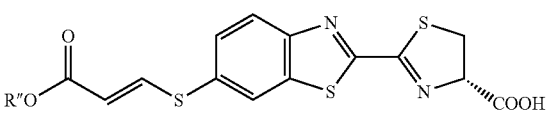

1-9
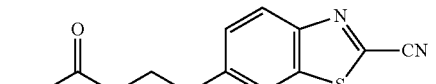

1-10
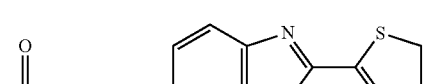

1-11
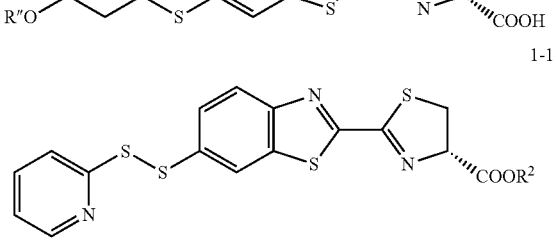

1-12
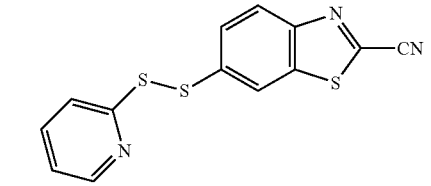

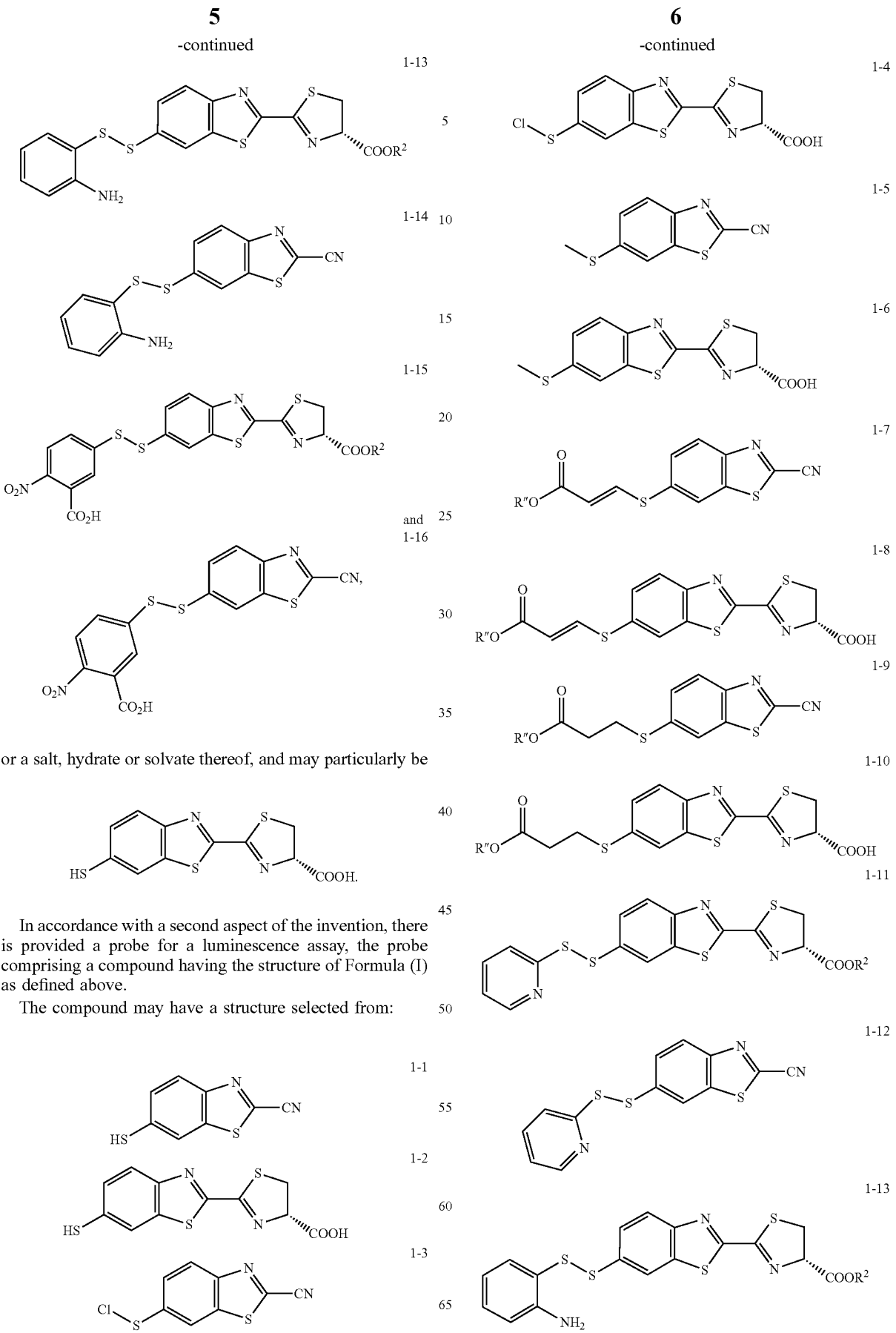
or a salt, hydrate or solvate thereof, and may particularly be
In accordance with a second aspect of the invention, there is provided a probe for a luminescence assay, the probe comprising a compound having the structure of Formula (I) as defined above.
The compound may have a structure selected from:

-continued 1-14
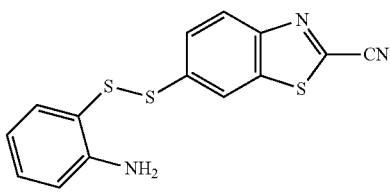

1-15
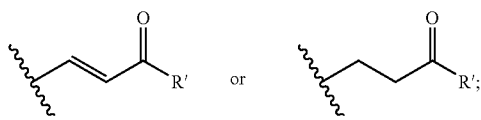

and
1-16
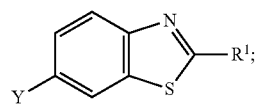

or a salt, hydrate or solvate thereof.

In accordance with a third aspect of this invention, there is provided a luciferase substrate comprising a compound having the structure of Formula (I) as defined above.

In accordance with a fourth aspect of this invention, there is provided a kit for a luminescence assay, the kit comprising a compound having the structure of Formula (I) as defined above and optionally one or more components selected from the group consisting of a luciferase enzyme having an amino acid sequence that has at least 80% sequence identity with SEQ ID NO: 1 or to any subsequence thereof, ATP, coenzyme A and $Mg^{2+}$.

In accordance with a fifth aspect of this invention, there is provided a method of biological imaging, the method comprising contacting, or causing to be contacted, a compound having the structure of Formula (I) as defined above with a luciferase enzyme having an amino acid sequence that has at least 80% sequence identity with SEQ ID NO: 1 or with any subsequence thereof in a subject or biological sample, and detecting a fluorescence or luminescence signal resulting from the contact.

The fluorescence or luminescence signal may be between 400 and 800 nm, between 500 and 700 nm or between 580 and 620 nm.

In accordance with a sixth aspect of this invention, there is provided a method of synthesising a compound having the structure of Formula (II):

Formula (II)
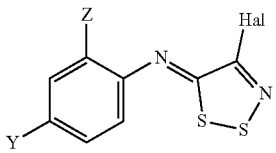

wherein:
$R^1$ is CN or

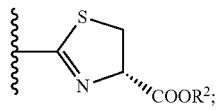

$R^2$ is H or optionally substituted alkyl;
Y is H, halogen, —$SR^a$, —$NR^bR^c$, —$NO_2$, —$N_3$, —$OR^d$;
$R^a$ is H, halogen, —$SR^3$, optionally substituted alkyl, optionally substituted haloalkyl, optionally substituted cycloalkyl, optionally substituted heterocyclyl, acyl,

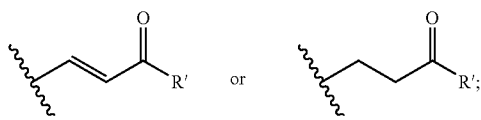

$R^3$ is optionally substituted alkyl, optionally substituted haloalkyl, optionally substituted cycloalkyl, optionally substituted heterocyclyl, optionally substituted aryl or optionally substituted heteroaryl;
$R^b$=$R^c$=H, or $R^b$=H and $R^c$=optionally substituted alkyl or optionally substituted aryl;
$R^d$ is H, optionally substituted alkyl, optionally substituted haloalkyl, optionally substituted cycloalkyl, optionally substituted heterocyclyl, optionally substituted aryl or optionally substituted heteroaryl;
R' is H, optionally substituted alkyl, optionally substituted aryl or OR"; and
R" is H, optionally substituted alkyl or optionally substituted aryl; or a salt, hydrate or solvate thereof;
the method comprising the steps of:
(i) reacting a compound having the structure of Formula (III):

Formula (III)
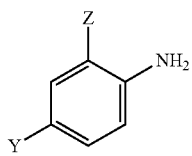

wherein Z is Cl, Br or I, and Y is as defined for Formula (II), with a 1,2,3-dithiazole in a suitable solvent to yield a compound having the structure of Formula (IV):

Formula (IV)
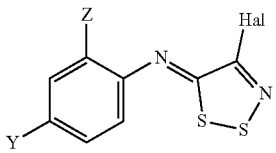

where Hal is a halogen; and
(ii) reacting the compound obtained in step (i) with a base selected from the group consisting of amidine bases [such as 1,8-diazabicyclo[5.4.0]undec-7-ene (DBU)

and 1,5-diazabicyclo[4.3.0]non-5-ene (DBN)], imidazole, alkali metal alkoxide bases, guanidine bases, 1,4-diazabicyclo[2.2.2]octane (DABCO), diisopropylethylamine (DIPEA), 2,6-di-tert-butylpyridine and phosphazene bases, to yield a compound having the structure of Formula (V):

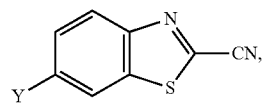

Formula (V)

and (iii) optionally reacting the compound obtained in step (ii) with D-cysteine or an alkyl ester thereof to yield a compound of Formula (II) where $R^1$ is

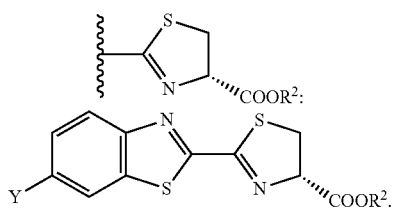

The 1,2,3-dithiazole may have the structure of Formula (VI):

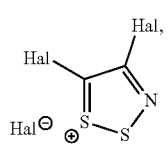

Formula (VI)

where each Hal is a halogen independently selected from Cl and Br.

The base may be DBU or DBN.

Y may be —$SR^a$, $R^a$ may be —$SR^3$, and $R^3$ may be

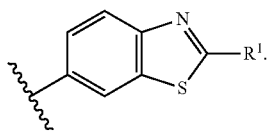

$R^2$ may be H or optionally substituted benzyl (Bn).

The method may further comprise a step of reacting the compound of Formula (II), where Y is a halogen, with a cross-coupling reagent and a thiolating agent to form a compound having the structure of Formula (VII):

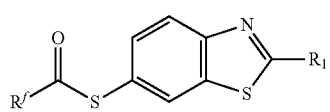

Formula (VII)

wherein $R^f$ is an optionally substituted alkyl or optionally substituted aryl.

The method may still further comprise a step of reacting the compound of Formula (VII) with one or more deacylating reagents to form a compound having the structure of Formula (VIII):

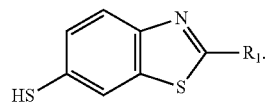

Formula (VIII)

The method may comprise a step of reacting a compound of Formula (XII):

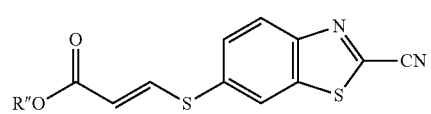

Formula (XII)

with a thiolate, alkoxide or D-cysteine to produce a compound of Formula (XV):

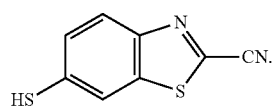

Formula (XV)

The method may comprise a step of reacting a compound of Formula (XII):

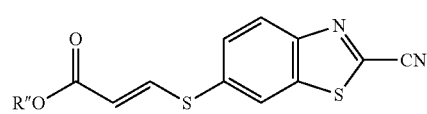

Formula (XII)

with D-cysteine to produce D-thioluciferin:

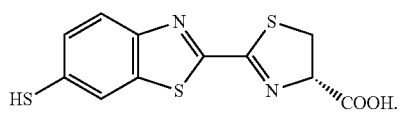

In accordance with a seventh aspect of this invention, there is provided a method of synthesising a compound having the structure of Formula (I):

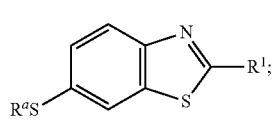

Formula (I)

wherein:
R¹ is CN or

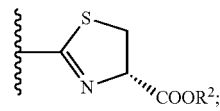

R² is H or optionally substituted alkyl;
Rᵃ is H, halogen, —SR³, optionally substituted alkyl, optionally substituted haloalkyl, optionally substituted cycloalkyl, optionally substituted heterocyclyl, acyl,

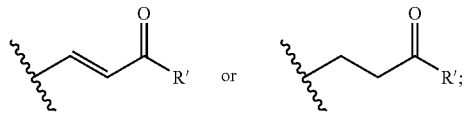

R³ is optionally substituted alkyl, optionally substituted haloalkyl, optionally substituted cycloalkyl, optionally substituted heterocyclyl, optionally substituted aryl or optionally substituted heteroaryl;
R' is H, optionally substituted alkyl, optionally substituted aryl or OR''; and
R'' is H, optionally substituted alkyl or optionally substituted aryl; or a salt, hydrate or solvate thereof;
the method comprising the steps of:
(i) reacting a compound having the structure of Formula (XVI):

Formula (XVI)

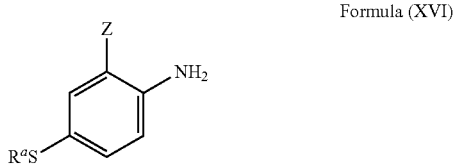

wherein Z is Cl, Br or I, with a 1,2,3-dithiazole in a suitable solvent to yield a compound having the structure of Formula (XVII)

Formula (XVII)

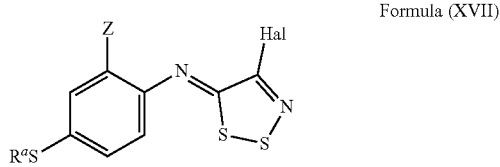

where Hal is a halogen; and
(ii) reacting the compound obtained in (i) with a base selected from the group consisting of amidine bases [such as 1,8-diazabicyclo[5.4.0]undec-7-ene (DBU) and 1,5-diazabicyclo[4.3.0]non-5-ene (DBN)], imidazole, alkali metal alkoxide bases, guanidine bases, 1,4-diazabicyclo[2.2.2]octane (DABCO), diisopropylethylamine (DIPEA), 2,6-di-tert-butylpyridine and phosphazene bases, to yield a compound having the structure of Formula (I) where R¹ is CN:

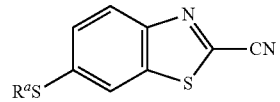

and
(iii) optionally reacting the compound obtained in (ii) with D-cysteine or an alkyl ester thereof to yield a compound of Formula (I) where R¹ is

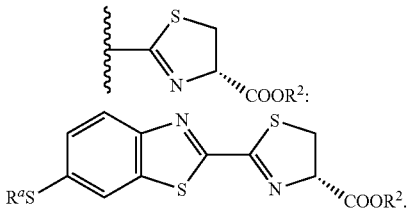

An embodiment of the invention will now be described, by way of example only, with reference to the accompanying drawings.

DETAILED DESCRIPTION OF THE INVENTION

Figure 1:
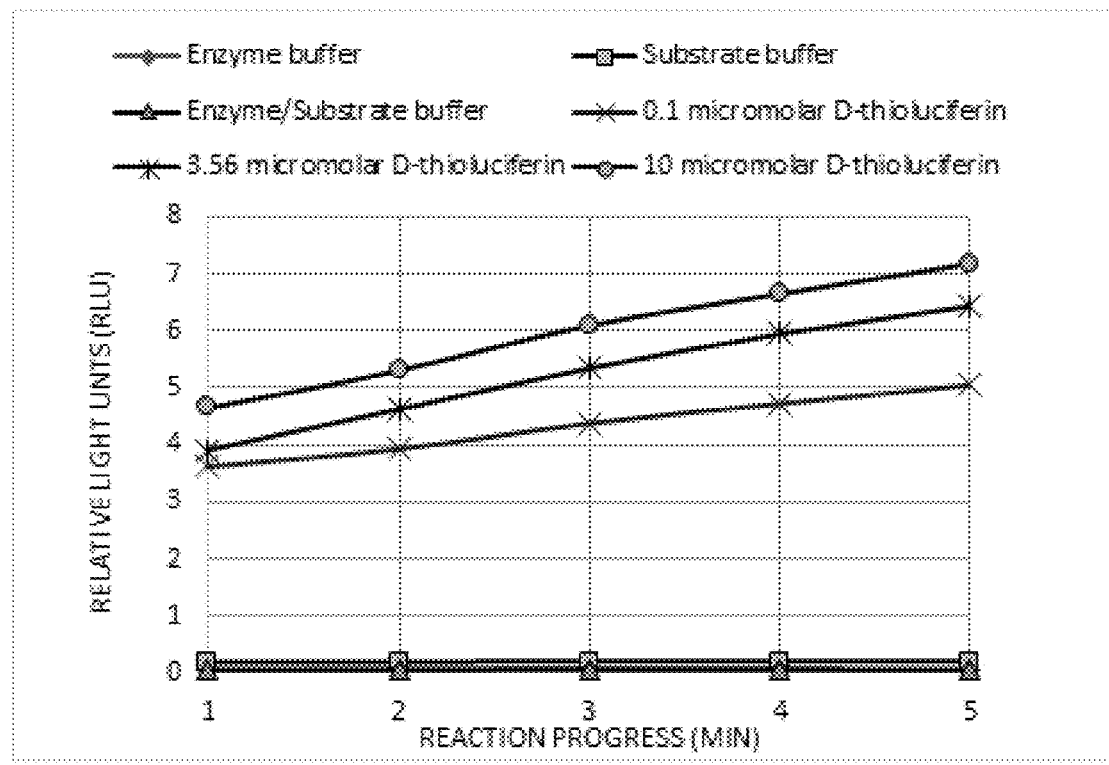
FIG. 1 is a graph illustrating kinetic profiles of D-thioluciferin treated with purified wild type (WT) luciferase (*Photinus pyralis* (luciferase) [Ppy Luc]). Purified enzyme (10 nM final) was rapidly combined with substrate (0.1, 10, 3.56 and 100 μM final concentration). Light emission was recorded every minute for 5 minutes, 1 minute post-injection. Background luminescent signal in the absence of substrate, enzyme and ATP are shown for reference. The assays were performed in triplicate and are represented as the mean.
Figure 2:
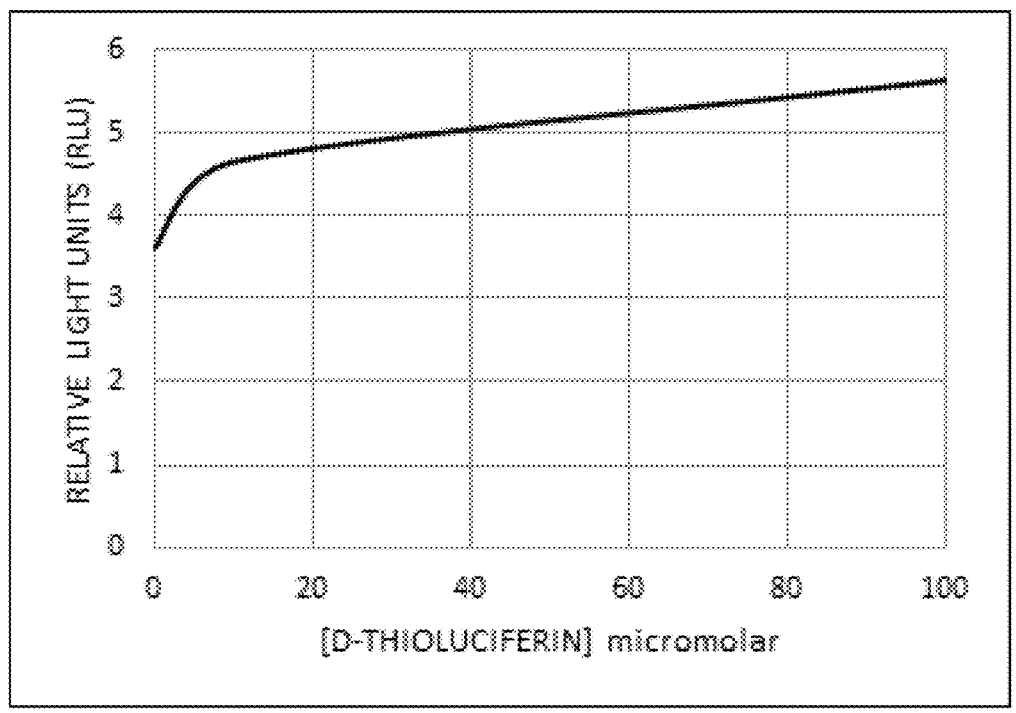
FIG. 2 is a graph illustrating relative light units (RLU) generated when WT luciferase (Ppy Luc) was treated with increasing concentrations of D-thioluciferin. D-Thioluciferin was added to purified enzyme (10 nM final) and light emission was recorded as a single reading 1 minute post-addition.
Figure 3:
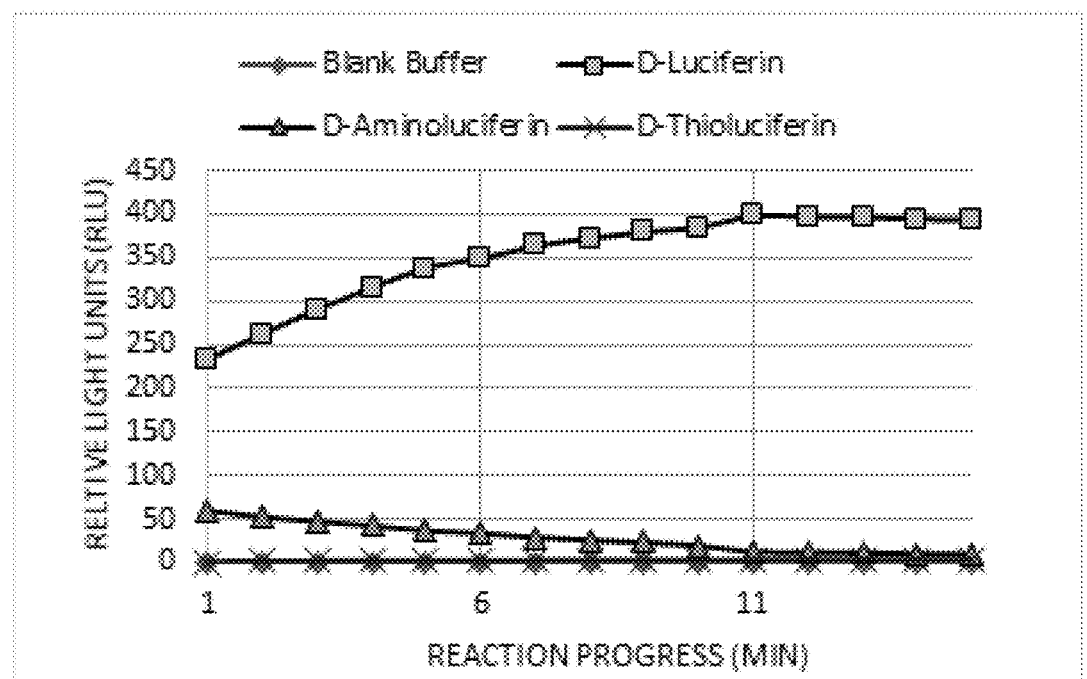
FIG. 3 is a graph illustrating comparative luminescence (in RLU) of D-luciferin, D-aminoluciferin and D-thioluciferin treated with WT luciferase (Ppy Luc). Luciferin 0.1 μM was added to purified enzyme (10 nM final) and light emission was recorded every minute 1 minute post-addition.
Figure 4:
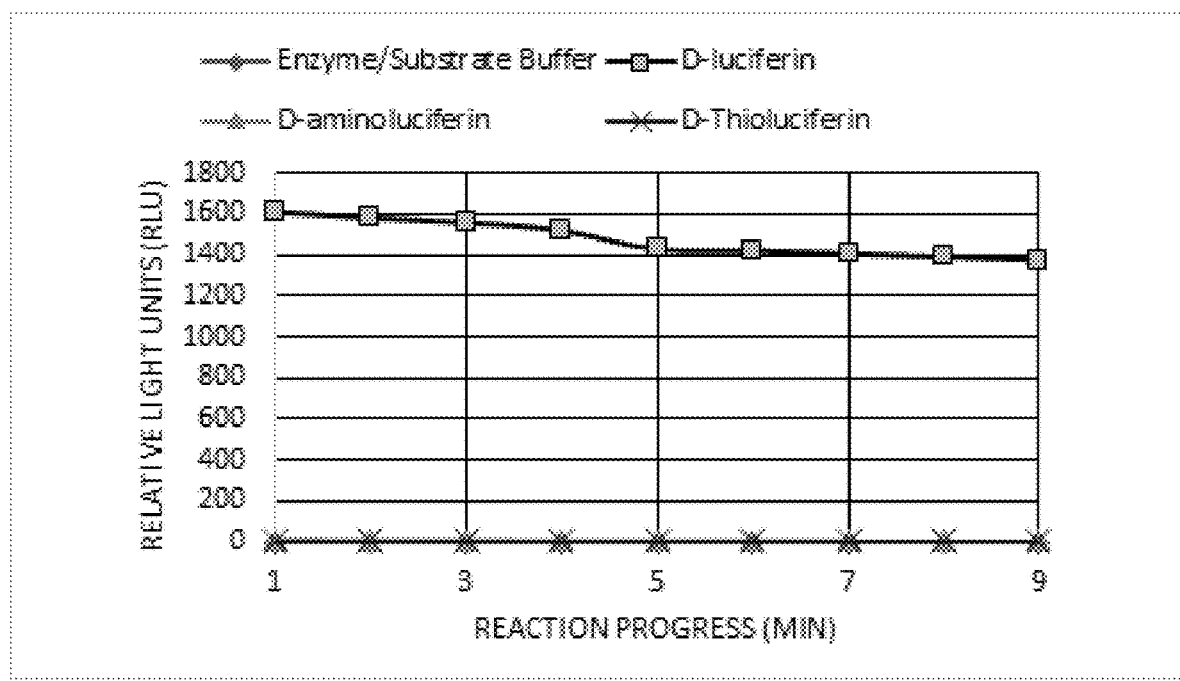
FIG. 4 is a graph illustrating comparative luminescence of D-luciferin, D-aminoluciferin and D-thioluciferin treated with WT luciferase (Ppy Luc). Luciferin 0.36 μM was added to purified enzyme (10 nM final) and light emission was recorded every minute 1 minute post-addition.
Figure 5:
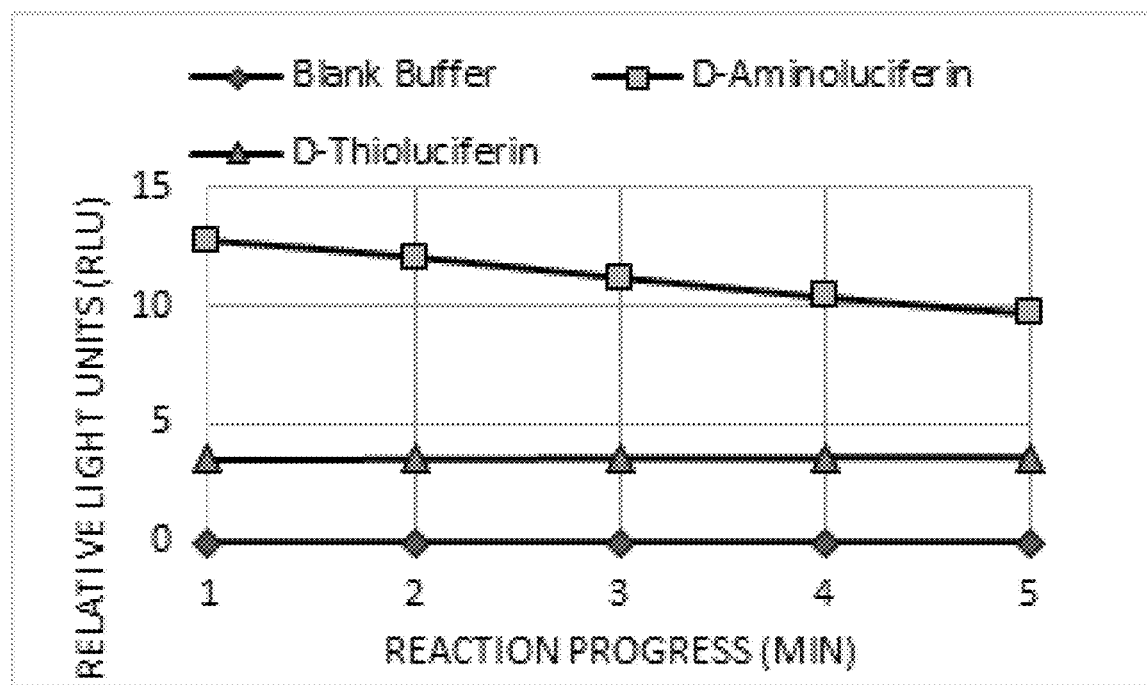
FIG. 5 is a graph illustrating comparative luminescence of D-aminoluciferin and D-thioluciferin treated with WT luciferase (Ppy Luc). Luciferin 0.1 μM was added to purified enzyme (10 nM final) and light emission was recorded as a single reading 5 minutes post-addition.
Figure 6:
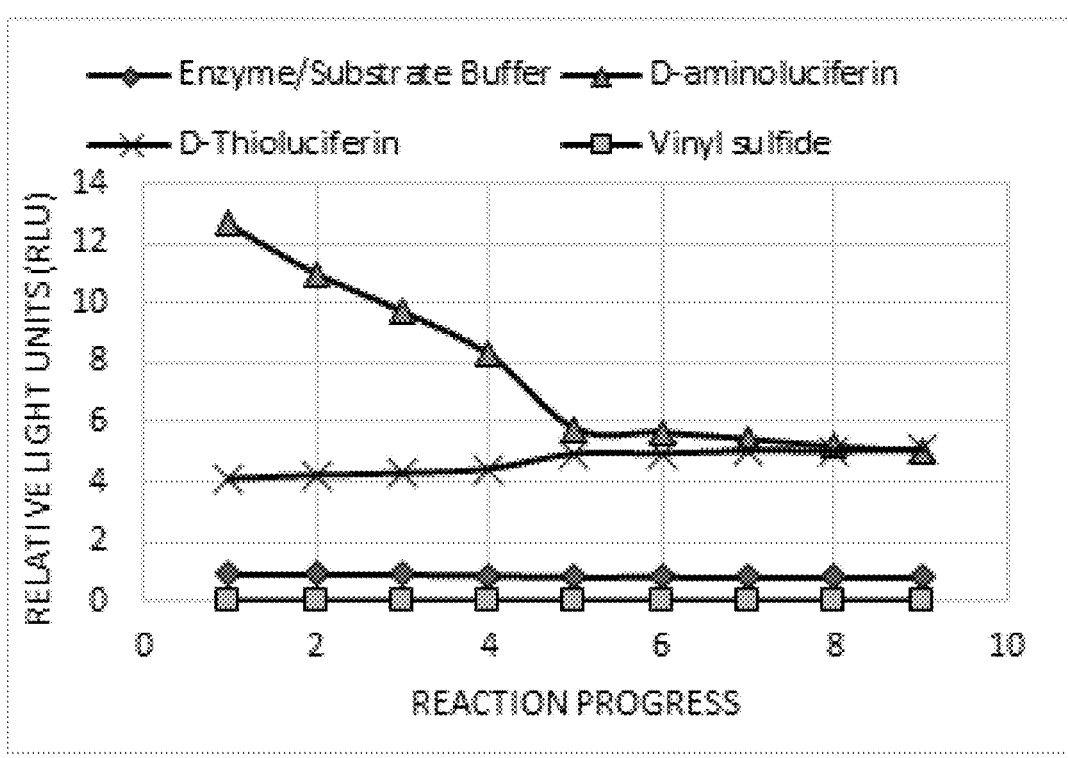
FIG. 6 is a graph illustrating comparative luminescence of D-aminoluciferin, D-thioluciferin and D-thioluciferin-vinylsulfide treated with WT luciferase (Ppy Luc). Luciferin 0.1 μM was added to purified enzyme (10 nM final) and light emission was recorded as a single reading 1 minute post-addition.

The invention provides thio derivatives of D-luciferin, also referred to as D-thioluciferin. The invention also provides methods for synthesising D-luciferin, its derivatives, and their related 2-cyanobenzothiazole precursors, all of which are commercially valuable because of their application in optical imaging. The luciferins and their derivatives can typically be used as probes in luminescence assays in combination with luciferase enzymes.

Throughout the specification and claims unless the content requires otherwise the word 'comprise' or variations such as 'comprises' or 'comprising' will be understood to imply the inclusion of a stated integer or group of integers but not the exclusion of any other integer or group of integers.

In the chemical structures presented, a wavy line denoted by "⧹⧸" and bisected by a bond indicates the site of attachment of a molecular fragment to a position on a molecule denoted by a reference letter such as $R^1$, $R^2$, $R^3$, $R^a$, $R^b$, $R^c$ etc. This is distinguished from a wavy line attached at an end thereof to a double bond, which indicates a mixture of E/Z isomers of the double bond.

Whenever the term "halogen" is used, that substituent can be any one of F, Cl, Br or I.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec_butyl, tert_butyl, pentyl, isopentyl, hexyl, etc. Alkyl groups can be substituted or unsubstituted. Substituted alkyl groups include arylalkyl groups, such as optionally substituted benzyl (Bn).

The abbreviations "Me", "Et", "Pr", and "Bu" refer to alkyl groups consisting of one, two, three and four carbon atoms, respectively, as is commonly known in the art. The prefix "i" preceding Pr or Bu refers to isopropyl or isobutyl, and the prefix 'T' or "tert" refers to "tertiary", e.g. tertiary butyl or tertiary octyl.

"Haloalkyl" refers to alkyl, as defined above, where some or all of the hydrogen atoms are replaced with halogen atoms. As for the alkyl group, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethane includes 1,1,1-trifluoromethyl.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Heterocyclyl" or "heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be substituted or unsubstituted.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, N-oxide, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinolone and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

"Luminescence" refers to the production of visible light occurring as a result of a chemical reaction (also termed "chemiluminescence"). Such chemical reactions typically occur between a luminescent molecule (e.g. luciferin) and an activating agent (e.g. luciferase enzyme).

"Bioluminescence" refers to luminescence resulting from biological sources and is typically caused by chemical reactions in living organisms or involving biological reagents (such as enzymes). Fireflies, for example, glow by bioluminescence.

"Fluorescence" occurs when electromagnetic radiation (light) is absorbed from an external excitation source by a fluorescent molecule (termed a fluorophore) and subsequently emitted. Fluorescence generally produces light of a frequency that is lower than, but otherwise independent of, the frequency of the absorbed light.

"Identity" as used herein means the identity between two amino acid sequences compared to each other within a corresponding sequence region having approximately the same amount of amino acids. For example, the identity of a full-length sequence of two amino acid sequences may be determined. Furthermore, a shorter amino acid sequence can be compared with a longer sequence and the identity between the two sequences will relate to the identity between the short sequence and a section of the longer sequence of approximately the same number of amino acids. In this way the identity of a truncated fragment of a luciferase polypeptide can be compared to a full luciferase polypeptide over the length of the truncated fragment. The amino acid sequences to be compared may differ in several positions which do not alter the biological function or structure of the polypeptides. Such "variants" may include amino acid substitutions, deletions, combinations or insertions of one or more positions in the amino acid sequences, but they still function in a substantially similar manner to the protein defined in SEQ ID NO: 1.

The term "subsequence" means a fragment or part of a full length sequence, such as an amino acid sequence. A subsequence of a luciferase amino acid sequence has one or more amino acids less than the full length luciferase amino acid sequence (e.g. one or more internal or terminal amino acid deletions from either the N- or C-terminal). Subsequences therefore can be any length up to the full length native molecule, provided the length is at least one amino acid less than the full length native molecule. Subsequences can vary in size.

The compounds according to the present disclosure have the structure of Formula (I):

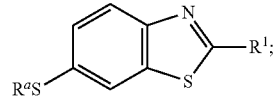

Formula (I)

wherein:

R$^1$ is CN or

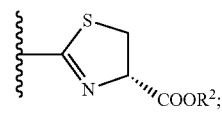

R$^2$ is H or optionally substituted alkyl;

R$^a$ is H, halogen, —SR$^3$, optionally substituted alkyl, optionally substituted haloalkyl, optionally substituted cycloalkyl, optionally substituted heterocyclyl, acyl,

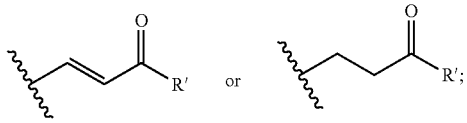

R³ is optionally substituted alkyl, optionally substituted haloalkyl, optionally substituted cycloalkyl, optionally substituted heterocyclyl, optionally substituted aryl or optionally substituted heteroaryl;
R' is H, optionally substituted alkyl, optionally substituted aryl or OR''; and
R'' is H, optionally substituted alkyl or optionally substituted aryl; or are salts, hydrates or solvates thereof.

Compounds in which $R^1$ is CN can be converted to their corresponding derivative in which $R^1$ is

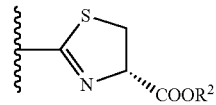

by reaction with D-cysteine. The $R^2$ group may either be H, in which the reactive acid group is free, or an optionally substituted alkyl group, in which the acid group is in the form of a protected ester. The protective ester can be hydrolysed by standard methods to liberate the reactive acid form.

In specific embodiments, $R^2$ is H, methyl, ethyl or benzyl, and the $R^a$ group is H, halogen, —$SR^3$ or optionally substituted alkyl. In some embodiments, $R^a$ is

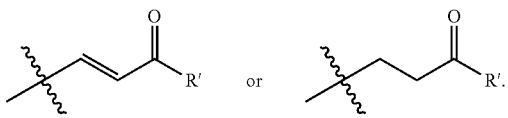

In other embodiments, $R^a$ is —$SR^3$ and $R^3$ is

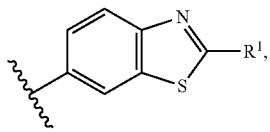

that is, a homodisulfide.

Exemplary compounds according to Formula (I) can be selected from the group provided in Table 1 below.

TABLE 1

Structures of selected compounds according to Formula (I)

| | |
|---|---|
| ![1-1] | 1-1 |
| ![1-2] | 1-2 |
| ![1-3] | 1-3 |
| ![1-4] | 1-4 |
| ![1-5] | 1-5 |
| ![1-6] | 1-6 |
| ![1-7] | 1-7 |
| ![1-8] | 1-8 |
| ![1-9] | 1-9 |
| ![1-10] | 1-10 |
| ![1-11] | 1-11 |
| ![1-12] | 1-12 |
| ![1-13] | 1-13 |
| ![1-14] | 1-14 |
| ![1-15] | 1-15 |

TABLE 1-continued

Structures of selected compounds according to Formula (I)

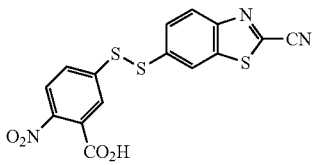

1-16

The compounds of Formula (I) can be substrates of a luciferase enzyme. *Photinus pyralis* (Common eastern firefly) luciferase has the amino acid sequence provided below in Table 2 as SEQ ID NO: 1. This sequence can also be found on the Uniprot online protein database under reference number Q27758, accessible at https://www.uniprot.org/uniprot/Q27758.

TABLE 2

Amino acid sequence of firefly luciferase isolated from *Photinus pyralis* (common eastern firefly)

|  | 10 | 20 | 30 | 40 |
|---|---|---|---|---|
|  | MEDAKNIKKG | PAPFYPLEDG | TAGEQLHKAM | KRYALVPGTI |
|  | 50 | 60 | 70 | 80 |
|  | AFTDAHIEVN | ITYAEYFEMS | VRLAEAMKRY | GLNTNHRIVV |
|  | 90 | 100 | 110 | 120 |
|  | CSENSLQFFM | PVLGALFIGV | AVAPANDIYN | ERELLNSMNI |
|  | 130 | 140 | 150 | 160 |
|  | SQPTVVFVSK | KGLQKILNVQ | KKLPIIQKII | IMDSKTDYQG |
|  | 170 | 180 | 190 | 200 |
|  | FQSMYTFVTS | HLPPGFNEYD | FVPESFDRDK | TIALIMNSSG |
|  | 210 | 220 | 230 | 240 |
|  | STGSPKGVAL | PHRTACVRFS | HARDPIFGNQ | IIPDTAILSV |
|  | 250 | 260 | 270 | 280 |
|  | VPFHHGFGMF | TTLGYLICGF | RVVLMYRFEE | ELFLRSLQDY |
|  | 290 | 300 | 310 | 320 |
|  | KIQSALLVPT | LFSFFAKSTL | IDKYDLSNLH | EIASGGAPLS |
|  | 330 | 340 | 350 | 360 |
|  | KEVGEAVAKR | FHLPGIRQGY | GLTETTSAIL | ITPEGDDKPG |
|  | 370 | 380 | 390 | 400 |
|  | AVGKVVPFFE | AKVVDLDTGK | TLGVNQRGEL | CVRGPMIMSG |
|  | 410 | 420 | 430 | 440 |
|  | YVNDPEATNA | LIDKDGWLHS | GDIAYWDEDE | HFFIVDRLKS |
|  | 450 | 460 | 470 | 480 |
|  | LIKYKGCQVA | PAELESILLQ | HPNIFDAGVA | GLPGDDAGEL |
|  | 490 | 500 | 510 | 520 |
|  | PAAVVVLEHG | KTMTEKEIVD | YVASQVTTAK | KLRGGVVFVD |
|  | 530 | 540 | 550 |  |
|  | EVPKGLTGKL | DARKIREILI | KAKKGGKSKL |  |

In some embodiments, luciferase enzymes can have amino acid sequences that have at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with SEQ ID NO: 1 or with any subsequence thereof.

The compounds of Formula (I) are characterised in that when they react as luciferase substrates, they generate detectable luminescence. The wavelength of luminescence emitted is in the range of 400 to 800 nm, between 500 and 700 nm or between 580 and 620 nm, with a maximum at about 600 nm. As such, the compounds of Formula (I) can be used as probes in luminescence assays. The probe may preferably have a chemical structure selected from the compounds presented in Table 1. The compounds or probes can be provided in a kit form, optionally together with one or more components selected from the group consisting of a luciferase enzyme having an amino acid sequence that has at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with SEQ ID NO: 1 or with any subsequence thereof, ATP, coenzyme A and $Mg^{2+}$ (e.g. magnesium carbonate, magnesium chloride, magnesium citrate, magnesium hydroxide (milk of magnesia), magnesium oxide, magnesium sulfate, and magnesium sulfate heptahydrate (Epsom salts)). The kit may be provided with instructions on how to use the probes in bioluminescence assays.

The invention also provides a method of biological imaging. In a typical embodiment, the method comprises contacting, or causing to be contacted, a compound having the structure of Formula (I), as defined above, with a luciferase enzyme in a subject or biological sample to be imaged, and detecting a fluorescence or luminescence signal resulting from the contact. The luciferase enzyme may have an amino acid sequence that has at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with SEQ ID NO: 1 or with any subsequence thereof. The subject may be a mammalian subject, such as a human, mouse or rat. The fluorescence or luminescence signal may be between 400 and 800 nm, between 500 and 700 nm or between 580 and 620 nm, and may be detectable by any suitable detector (such as a fluorometer or luminometer).

In an alternative embodiment, the method may include applying light, typically of a frequency of between 300 and 800 nm, between 350 and 450 nm, or between 380 and 420 nm (preferably at about 390 nm), to a subject or biological sample to which a compound having the structure of Formula (I) has been administered, and detecting a fluorescence signal emitted from the subject or biological sample resulting from excitation of the compound by the light.

The invention also provides methods for synthesising D-luciferin, derivatives of D-luciferin, and related 2-cyanobenzothiazoles. The method can be used to synthesise compounds having the structure of Formula (II)

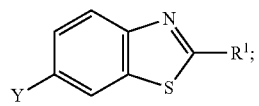

Formula (II)

wherein:

$R^1$ is CN or

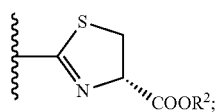

$R^2$ is H or optionally substituted alkyl;
Y is H, halogen, —$SR^a$, —$NR^bR^c$, —$NO_2$, —$N_3$, —$OR^d$;
$R^a$ is H, halogen, —$SR^3$, optionally substituted alkyl, optionally substituted haloalkyl, optionally substituted cycloalkyl, optionally substituted heterocyclyl, acyl,

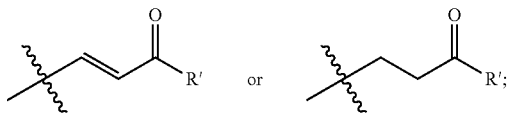 or $R^3$ is optionally substituted alkyl, optionally substituted haloalkyl, optionally substituted cycloalkyl, optionally substituted heterocyclyl, optionally substituted aryl or optionally substituted heteroaryl;
$R^b$=$R^c$=H, or $R^b$=H and $R^c$=optionally substituted alkyl or optionally substituted aryl;
$R^d$ is H, optionally substituted alkyl, optionally substituted haloalkyl, optionally substituted cycloalkyl, optionally substituted heterocyclyl, optionally substituted aryl or optionally substituted heteroaryl;
R' is H, optionally substituted alkyl, optionally substituted aryl or OR"; and
R" is H, optionally substituted alkyl or optionally substituted aryl; or a salt, hydrate or solvate thereof.

The method comprises the steps of:
(i) reacting a compound having the structure of Formula (III)

Formula (III)

wherein Z is Cl, Br or I, and Y is as defined for Formula (II), with a 1,2,3-dithiazole in a suitable solvent to yield a compound having the structure of Formula (IV)

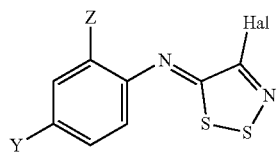

Formula (IV)

where Hal is a halogen selected from Cl and Br;
(ii) reacting the compound of Formula (IV) with a base to yield a compound having the structure of Formula (V)

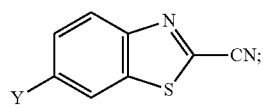

Formula (V)

and
(iii) optionally reacting the compound of Formula (V) with D-cysteine or an alkyl ester thereof to yield a compound of Formula (II) where $R^1$ is

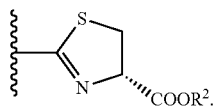

The method can particularly be used to synthesise the compounds of Formula (I).
The 1,2,3-dithiazole of step (i) can have the structure of Formula (VI)

Formula (VI)

where each Hal is a halogen independently selected from Cl and Br. In a preferred embodiment, the 1,2,3-dithiazole is Appel's salt, in which each Hal is a Cl, which has the following structure

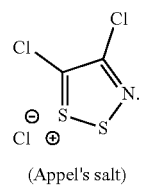

(Appel's salt)

The base of step (ii) can be selected from the group consisting of amidine bases [such as 1,8-diazabicyclo[5.4.0]undec-7-ene (DBU) and 1,5-diazabicyclo[4.3.0]non-5-ene (DBN)], 1,4-diazabicyclo[2.2.2]octane (DABCO), diisopropylethylamine (DIPEA), 2,6-di-tert-butylpyridine, imidazole, alkali metal alkoxide bases (e.g. NaOMe, NaOEt, NaOPr NaOBu, KOMe, KOEt, KOPr and KOBu), guanidine bases, and phosphazene bases (e.g. e.g. $P_1$-t-Bu [tert-butylimino-tri(pyrrolidino)phosphorene], BEMP, $P_1$-t-Oct, $P_2$-Et, $P_2$-t-Bu, $P_2$—F, $P_4$-t-Bu, $P_4$-t-Oct, or $P_5$—F. Preferably, the base is DBU or DBN.

The use of the aforementioned bases, and particularly DBU and DBN, allows the synthesis to be carried out in a one-pot reaction without the use of a metal catalyst. Most known methods of synthesising luciferins require a metal catalyst [e.g. Pt(II), Cu(I) or Cu(II)] and elevated temperatures to oxidatively cyclise a substituted aniline intermediate into a substituted 2-cyanobenzothiazole. Other methods employ a combination of fragmentation and electrocyclisation to form the substituted 2-cyanobenzothiazole. However, in the method of the present invention, the mild bases described above, act to first fragment and then cyclise the dithiazole of Formula (IV) into the 2-cyanobenzothiazole of Formula (V) in a one-pot base-mediated $S_N2$ Ar mechanism, which can conveniently be carried out at room temperature. This mechanism has a high degree of functional group tolerability and permits a greater range of luciferins to be accessed than the known electrocyclisation and oxidative coupling methods, which are limited in that they do not tolerate electron withdrawing substituents on the aniline.

In some embodiments, $R^2$ can be H, methyl, ethyl or benzyl.

The method may include one or more additional steps or transformations for introducing a sulfur atom at the 6-position of the benzothiazole ring.

In some preferred embodiments, Y is —SR$^a$. R$^a$ can be —SR$^3$ and R$^3$ can be

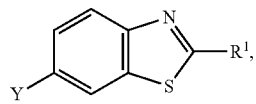

a homodisulfide of a 6-thioluciferin derivative.

In some embodiments, the method can include reacting a compound of Formula (II), where Y is a halogen selected from F, Cl, Br and I, with a cross-coupling reagent and a thiolating agent to form a compound having the structure of Formula (VII)

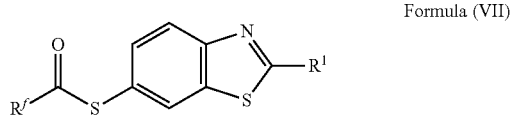

Formula (VII)

wherein R$^f$ is an optionally substituted alkyl or optionally substituted aryl.

The method can further include reacting the compound of Formula (VII) with one or more deacylating reagents to form a compound having the structure of Formula (VIII)

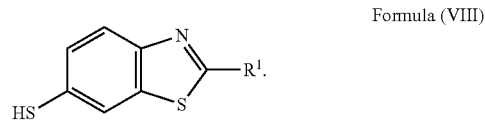

Formula (VIII)

Any suitable deacylating reagents can be used. Metal alkoxides in alcohol are particularly useful for this purpose, with sodium methoxide in methanol being a preferred example.

The method of the present invention involves a fragmentation cyclization process in which the 2-cyanobenzothiazole motif is constructed from the condensation of substituted aniline with 4,5-dihalo-1,2,3-dithiazolium halide (which in one embodiment is Appel's salt) to generate an N-arylimino-1,2,3-dithiazole which is subsequently fragmented and cyclised to afford the corresponding 2-cyanobenzothiazole of Formula (V), as shown in Scheme 2.

Scheme 2: Reagents and conditions: i) Appel's salt/DCM/1-2 h, ii) DBU/DCM/5° C., 3-4 h, iii a) PyHCl/DMF/150° C.,/1 h, iii b) Zn/NH$_4$Cl/MeOH/rt/20 min, iv) D-Cys/K$_2$CO$_3$/MeOH or CH$_3$CN:H$_2$O/rt/20 min-1 h

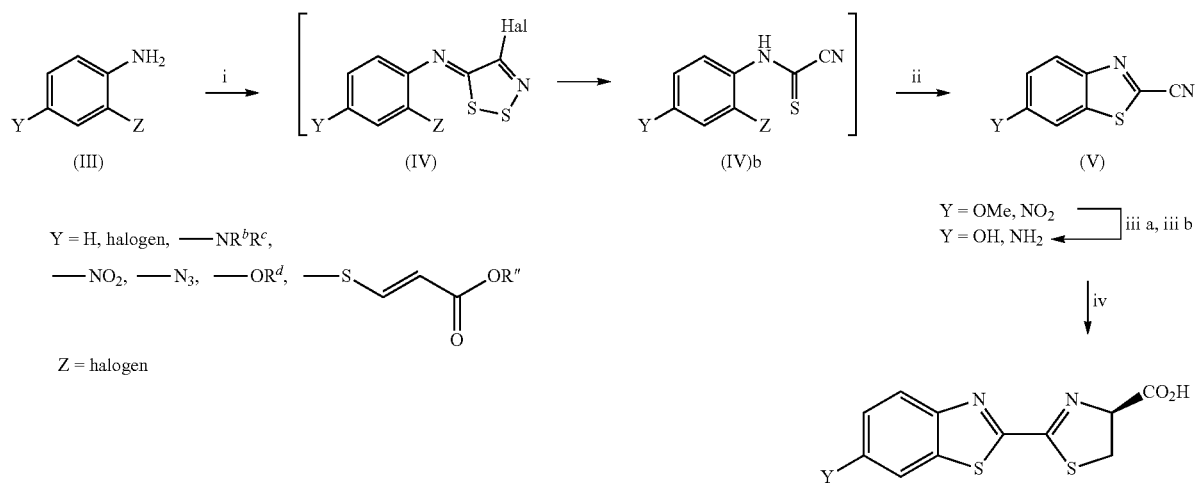

Known synthetic methods use a palladium(II)/copper(I) mediated oxidative ring cyclization of an aniline similar to Formula (III) but which has Z═H. This method is costly, carried out at elevated temperature, and may not be suitable for unprotected sulfur containing compounds as the sulfur groups can cause catalyst poisoning. The synthesis of 2-cyanobenzothiazoles provided here employs a base-mediated S$_N$2 Ar, metal-free cyclization via a substituted aniline (Scheme 2). This means of cyclisation allows for a shorter, scalable synthesis of D-luciferin and its derivatives which can conveniently be carried out at moderately low temperature.

Para-substituted anilines having a protected oxygen (-OPG, where PG=protecting group) at the 4-position (such as a p-methoxy, p-benzyloxy etc. group) can be converted into their corresponding 6-OPG-2-cyanobenzothiazoles, which can be deprotected to form 6-hydroxy-2-cyanobenzothiazole, the precursor of D-luciferin (see Scheme 2).

Similarly, anilines substituted with a para-nitro (—NO$_2$) functional group can be converted into the respective 6-nitro-2-cyanobenzothiazoles. Reduction of the nitro group leads to the 6-amino-2-cyanobenzothiazole (see Scheme 2).

Scheme 3: Synthesis of D-thioluciferin from 6-iodo-substituted 2-cyanobenzothiazole

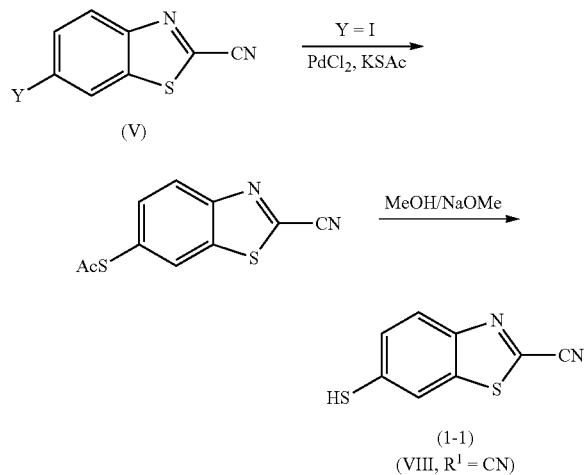

Furthermore, anilines substituted with a halogen (e.g. where Y is iodo), can be converted into their corresponding 6-halo-2-cyanobenzothiazoles. The halo groups can be substituted with thiols to provide novel 6-thio-2-cyanobenzothiazoles, which can be subsequently converted to the 6-thio-D-luciferins by reaction with D-cysteine, as illustrated in Scheme 3.

The synthesis of D-thioluciferin can be also be achieved starting with a 4-thio substituted aniline (Scheme 4).

Free thiol is usually too reactive in the presence of Appel's salt and not able to be used directly. It is therefore preferably protected as a vinylsulphide (X, Scheme 4). The vinylsulphide (X) can be transformed using methodology described above to form the 2-cyanobenzothiazole intermediate (XII). The resultant thioethers can be deprotected by reaction with a thiolate or alkoxide via a base-catalysed retro-Michael reaction. The vinylsulfide protected luciferin (XIII) is novel and has potential applications in thiol sensing. The vinylsulfide ester-protected 6-thio-2-cyanobenzothiazole (XII) is particularly useful since it can react specifically with D-cysteine to release bioluminescent D-thioluciferin.

The vinylsulfide ester-protected 6-thio-2-cyanobenzothiazole (XII) can also be synthesised from its ortho-halogenated aniline precursor. The vinylsulfide ester-protected 6-thio-2-cyanobenzothiazole (XII) can also be accessed by employing the base-mediated $S_N2$ Ar, metal-free cyclization described above in Scheme 2 for the preparation of 6-OPG-2-cyanobenzothiazoles and related 2-cyanobenzothiazoles.

The present synthetic method circumvents many of the problems associated with known methods of synthesising D-luciferin and related 6'-derivatives. In particular, the use of a metal-free synthesis to form the 2-cyanobenzothiazole core provides a considerable cost saving, which is particularly important for large scale synthetic processes. Furthermore, the present method has a reduced number of synthetic steps and a generally higher overall yield of 49% than the metal-catalysed syntheses, which have a generally low overall yield of only 9%.

The invention will now be described in more detail by way of the following non-limiting examples.

Scheme 4. Synthetic routes toward 6-thio-2-cyanobenzothiazole (1-1) and D-thioluciferin (1-2) using Appel's salt condensation and a vinylsulfide protecting group strategy.

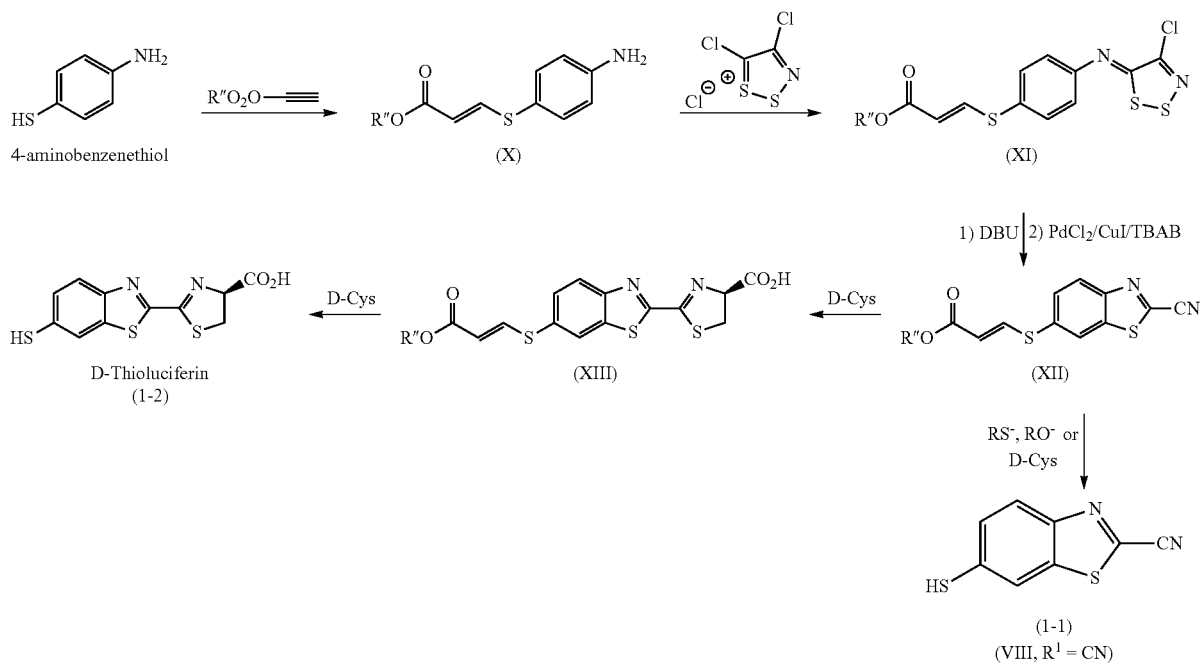

RS⁻ = thiolate
RO⁻ = alkoxide
D-Cy = D-cysteine

EXAMPLES

All reactions were carried out in oven-dried glassware under an inert nitrogen atmosphere, unless otherwise stated. Reagents were obtained from commercial sources and used as received unless otherwise stated. Solvents were evaporated under reduced pressure at 40° C. using a rotary evaporator, unless otherwise stated. Reaction temperatures were achieved with heat/silicone oil (for >25° C.), ice water/$NH_4Cl$ salt (for 0° C.), and acetone/liquid nitrogen (<−20° C.). Aqueous solutions were prepared using deionized water. All reactions were monitored by TLC using aluminium-backed silica-gel 60 F254 plates and/or Silica gel on TLC plates with fluorescent indicator 254 nm, and compounds were visualized on TLC under UV-lamp (ultraviolet) and/or were sprayed with a 2.5% solution of p-anisaldehyde in a mixture of sulphuric acid and ethanol (1:10 v/v), iodine vapour, ceric ammonium sulphate solution, or ninhydrin solution and then heated at 250° C. using a heat gun. Column chromatography was carried out using silica-gel (Silica Gel 60, 40-63 microns). Nuclear Magnetic Resonance (NMR) spectra were recorded on either a 400 MHz spectrometer ($^1$H at 399.95 MHz and $^{13}$C at 100.6 MHz), or a 300 MHz spectrometer ($^1$H at 300.08 MHz). Chemical shifts (δ) and J-coupling values were reported in units of ppm and Hz respectively. Chemical shifts for $^1$H and $^{13}$C were recorded using tetramethylthylsilane (TMS) as the internal standard. Elemental analyses were performed using a CHNS elemental analyzer. Infra-Red (IR) spectroscopy was performed on a FT-IR Spectrometer with vibrations measured in units of cm$^{-1}$. Melting points were obtained using a hot stage microscope (HSM) and are uncorrected. Mass Spectrometry (MS) determinations were carried out using electron impact (EI) on a GC instrument.

Synthesis of 4,5-dichloro-1,2,3-dithiazol-1-ium chloride (Appel's Salt)

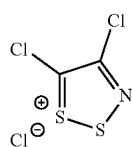

To a solution of chloroacetonitrile (2 mL, 31.60 mmol, 1.0 eq) in DCM (15 mL) at ambient temperature was added sulphur monochloride (13 mL, 158.01 mmol, 5.0 eq). Thereafter, the reaction mixture was allowed to stir for a minute and then left to stand for 18 h. The resulting brown precipitate that had formed was filtered under vacuum, and washed with DCM. The brown-green solid was then dried under vacuum (5.30 g, 80%). Mp: 117-130° C.

General Procedure for the One-Pot, Base-Mediated, Metal Free Synthesis of 6-Substituted 2-cyanobenzothiazoles from Monobrominated Para-Substituted Anilines Appel's salt and an aniline were allowed to stir in $CH_2Cl_2$ (DCM) for 1 h at room temperature under a nitrogen atmosphere. The solution was then cooled to below 5° C. and base (preferably DBU or DBN) was added, dropwise over 30 min, to the stirring solution maintained at 5° C., all under a nitrogen atmosphere. After the addition, the resulting mixture was stirred for 30 min while allowing it to warm to room temperature, after which it was refluxed at 40 C for 4 h. Upon cooling to room temperature (rt), ethyl acetate (EtOAc) was added. The reaction mixture was then washed with saturated $NH_4Cl_{aq}$ solution, and $H_2O$. The organic phase was dried over $Na_2SO_4$ and concentrated in vacuo. The crude material was purified by silica gel chromatography to provide the corresponding benzothiazoles.

2-Cyano-6-methoxybenzothiazole

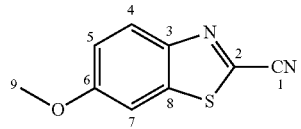

Following the above outlined procedure, Appel's salt (0.260 g, 1.24 mmol, 1 eq) and 2-bromo-4-methoxyaniline (0.250 g, 1.24 mmol, 1 eq) were combined and reacted with DBU (0.92 mL, 6.19 mmol, 5 eq) to afford 2-cyano-6-methoxybenzothiazole as a pale yellow solid (0.150 g, 64%). Mp: 129-130 C (lit. 129-131° C.). $^1$H-NMR (400 MHz, DMSO) δ 8.15 (1H, d, J=9.1 Hz, H-4), 7.89 (1H, d, J=2.4 Hz, H-7), 7.33 (1H, dd, J=9.1, 2.4 Hz, H-5), 3.93 (3H, s, H-9) ppm. $^{13}$C-NMR (400 MHz, DMSO) δ 160.4 (C-2), 146.7 (C-6), 138.3 (C-3), 134.1 (C-8), 125.8 (C-7), 119.1 (C-5), 114.1 (C-1), 106.0 (C-4), 56.52 (C-9) ppm. MS (ESI+): m/z Calculated for $C_9H_6N_2OS$ [M+H] 191.0279, found 191.0273.

2-Cyano-6-hydroxybenzothiazole

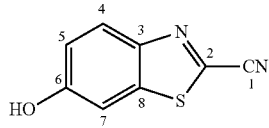

Pyridine hydrochloride (1.18 g, 10.2 mmol, 10 eq) and 6-methoxy-2-cyanobenzothiazole (0.195 g, 1.02 mmol, 1 eq) were combined in a rigorously dried sealed tube, purged and placed under an inert nitrogen atmosphere. The reaction mixture was then stirred at 180° C. for 1 h. The resulting red-brown residue was cooled to room temperature and then dissolved in EtOAc (20 mL) and washed with saturated $NaHCO_3$ (1×20 mL), 1M HCl (1×10 mL), $H_2O$ (4×10 mL), and brine (1×10 mL). The organic layer was dried over $MgSO_4$, filtered, and concentrated in vacuo. The crude product was purified using column chromatography eluting with 3:7 EtOAc:Hexane to yield 2-cyano-6-hydroxybenzothiazole as a pale yellow solid. Mp: 202-207° C. (lit. 205-207° C.). $^1$H-NMR (400 MHz, DMSO) δ 10.51 (1H, br s, —OH), 7.89 (1H, d, J=9.0 Hz, H-4), 7.60 (1H, d, J=2.4 Hz, H-7), 7.19 (1H, dd, J=9.1, 2.4 Hz, H-5) ppm. $^{13}$C-NMR (100.6 MHz, CDCl$_3$) δ 160.4 (C-2), 147.4 (C-6), 139.1 (C-3), 134.0 (C-8), 126.8 (C-7), 119.8 (C-5), 114.4 (C-1), 107.5 (C-4) ppm. MS (ESI+): m/z Calculated for $C_8H_4N_2OS$ [M+H] 177.0122, found 177.0117.

2-Cyano-6-nitrobenzothiazole

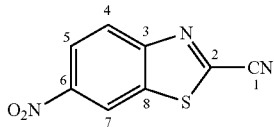

Following the above outlined procedure, Appel's salt (0.211 g, 1.01 mmol, 1.1 eq) and 2-bromo-4-nitroaniline (0.200 g, 0.921 mmol, 1 eq) were combined and reacted with DBU (0.70 mL, 4.61 mmol, 5 eq) to afford 2-cyano-6-nitrobenzothiazole as an orange solid (0.081 g, 43%). Mp: 118-119° C. $^1$H-NMR (400 MHz, CDCl$_3$) δ 8.97 (1H, dd, J=2.2, 0.5 Hz, H-7), 8.55 (1H, dd, J=9.6, 1.4 Hz, H-5), 8.42 (1H, dd, J=9.1, 1.4 Hz, H-4) ppm. $^{13}$C-NMR (100.6 MHz, CDCl$_3$) δ 155.3 (C-2), 147.3 (C-6), 141.8 (C-3), 135.6 (C-8), 126.1 (C-5), 123.0 (C-4), 118.6 (C-7), 114.0 (C-1) ppm. MS (ESI+): m/z Calculated for C$_8$H$_3$N$_3$O$_2$S [M+H] 206.0024, found 204.9715.

2-Cyano-fluorobenzothiazole

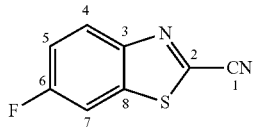

Following the above outlined procedure, Appel's salt (0.241 g, 1.16 mmol, 1.1 eq) and 2-bromo-4-fluoroaniline (0.200 g, 1.05 mmol, 1 eq) were combined and reacted with DBU (0.79 mL, 5.26 mmol, 5 eq) to afford 2-cyano-6-fluorobenzothiazole as a yellow solid (0.0870 g, 46%). Mp: 86-87° C. $^1$H-NMR (400 MHz, DMSO) δ 8.04 (1H, dd, J=8.0, 1.5 Hz, H-4), 7.64 (1H, dd, J=7.5, 5.0 Hz, H-7), 7.26 (1H, td, J=8.0, 1.5 Hz, H-5) ppm. $^{13}$C-NMR (100.6 MHz, DMSO) δ 158.5 (C-6), 147.2 (C-3) 136.7 (C-8), 138.1 (Ar—H), 123.8 (Ar—H), 113.8 (Ar—H), 113.2 (C-1), 108.9 (Ar—H) ppm.

2-Cyano-6-iodobenzothiazole

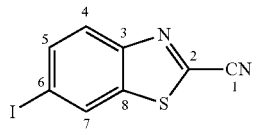

Following the above outlined procedure, Appel's salt (0.154 g, 0.738 mmol, 1.1 eq) and 2-bromo-4-iodoaniline (0.200 g, 0.671 mmol, 1 eq) were combined and reacted with DBU (0.50 mL, 3.35 mmol, 5 eq) to afford 6-iodo-2-cyanobenzothiazole as pale yellow solid (0.104 g, 54%). Mp: 131-132° C. $^1$H-NMR (400 MHz, DMSO) δ 8.52 (1H, d, J=8.0 Hz, H-4), 7.90 (1H, d, J=2.0 Hz, H-7), 7.43 (1H, dd, J=8.0, 2.1 Hz, H-5) ppm. $^{13}$C-NMR (100.6 MHz, DMSO) δ 150.5 (C-6), 136.7 (C-2), 136.4 (C-1), 133.2 (Ar-q), 131.9 (Ar-q), 123.2 (Ar-q), 113.3 (C-1), 92.1 (C-6) ppm. MS (ESI+): m/z Calculated for C$_8$H$_3$IN$_2$S [M+H] 286.9139, found 286.9134.

D-luciferin

Synthesis of (S)-2-(6-hydroxybenzo[d]thiazol-2-yl)-4,5-dihydrothiazole-4-carboxylate

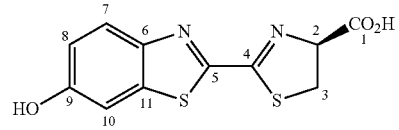

D-Cysteine hydrochloride monohydrate (30.0 mg, 0.171 mmol, 1.04 eq) and 2-cyano-6-hydroxybenzothiazole (29.0 mg, 0.163 mmol, 1 eq) were dissolved in 2:1 MeOH:H$_2$O (1 mL). The resulting solution was allowed to stir at room temperature for 5 min under a nitrogen atmosphere, after which potassium carbonate (23.0 mg, 0.164 mmol 1.01 eq) was added. The resulting bright yellow-green solution was allowed to stir for an additional 20 min, at room temperature, while maintaining the inert atmosphere. Upon consumption of 2-cyano-6-hydroxybenzothiazole, as evidenced by TLC analysis, the methanol was removed in vacuo and the remaining aqueous solution cooled to 0° C. and acidified to pH 3 with 3 M HCl. The aqueous layer was then extracted with EtOAc (5×10 mL) and the combined organics were dried over Na$_2$SO$_4$, filtered, concentrated in vacuo and purified with column chromatography 3:6:1 DCM:EtOAc:MeOH to provide D-luciferin as a pale yellow solid (39.0 mg, 86%). [α]20/D obs=−29°, DMF, c=1 ([α]20/D lit.=−34°, DMF, c=1).[3] Mp: 197-199° C. (lit. 196° C.).[3] $^1$H-NMR (400 MHz, MeOD) δ 7.93 (1H, d, J=8.9 Hz, H-7), 7.35 (1H, d, J=2.3 Hz, H-10), 7.10 (1H, dd, J=8.9, 2.3 Hz, H-8), 5.40 (1H, app t, J=9.0 Hz, H-2), 3.79 (2H, m, H-3) ppm. $^{13}$C-NMR (100.6 MHz, CDCl$_3$) δ 172.1 (C-1), 166.2 (C-4), 157.6 (C-9), 157.1 (C-5), 146.8 (C-6), 137.7 (C-11), 124.5 (C-7), 116.8 (C-10), 105.9 (C-8), 78.2 (C-2), 34.5 (C-3) ppm. HRMS (ESI+): m/z Calculated for C$_{11}$H$_8$N$_2$O$_3$S$_2$ [M+Na] 302.9874, found 302.9868.

D-aminoluciferin

Potassium (S)-2-(6-aminobenzo[d]thiazol-2-yl)-4,5-dihydrothiazole-4-carboxylate

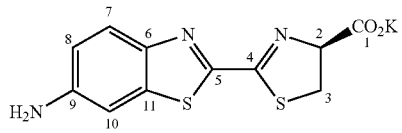

D-Cysteine hydrochloride monohydrate (81.2 mg, 0.462 mmol, 1.1 eq) and 6-amino-cyanobenzothiazole (71.0 mg, 0.405 mmol, 1 eq) were dissolved in 2:1 MeOH:H$_2$O (1 mL). The resulting solution was allowed to stir at room temperature for 5 min under a nitrogen atmosphere, after which potassium carbonate (56.5 mg, 0.409 mmol, 1.01 eq) was added. The resulting bright yellow-green solution was allowed to stir for an additional 40 min, while maintaining an inert atmosphere. Upon consumption of 6-amino-cyanobenzothiazole, as evidenced by TLC analysis, the reaction mixture was diluted with water (4 mL) and washed with EtOAc (1×4 mL). The aqueous was then reduced and the resulting precipitate was filtered and washed with cold MeOH (2×1 mL). The precipitate was then further purified using reverse phase chromatography eluting with a gradient of 0-90% MeOH in water to afford D-aminoluciferin potassium salt as a pale yellow solid (0.123 g, 96%). [α]20/D obs: −14° (H$_2$O, c=1). Mp: 111-123° C. $^1$H-NMR (400 MHz, D$_2$O) δ 8.32 (1H, d, J=8.8 Hz, H-7), 7.79 (1H, s, H-10), 7.55 (1H, d, J=8.0 Hz, H-8), 5.72 (1H, m, H-2), 3.8-4.2 (2H, m, H-3). HRMS (ESI+): m/z Calculated for C$_{11}$H$_9$N$_3$O$_2$S$_2$K [M+H] 317.9773, found 317.9768.

(S)-2-(6-aminobenzo[d]thiazol-2-yl)-4,5-dihydrothiazole-4-carboxylic acid

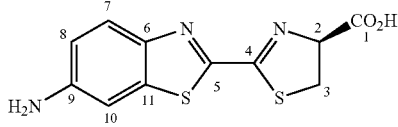

D-Aminoluciferin potassium salt (30.0 mg, 0.0950 mmol) was dissolved in water (1 mL). The solution was then cooled to 0° C. and acidified to pH 4 with 1 M HCl. The aqueous solution was then extracted with EtOAc (4×1 mL) and the organic extracts were combined, washed with brine (1×1 mL), dried over MgSO$_4$, filtered through Celite and concentrated in vacuo to afford the acid as a light yellow solid (10.0 mg, 37%). $^1$H-NMR (400 MHz, DMSO) δ 7.73 (1H, d, J=8.8 Hz, H-7), 7.07 (1H, d, J=2.2 Hz, H-10), 6.84 (1H, dd, J=8.8, 2.2 Hz, H-8), 5.70 (2H, s, —NH$_2$), 4.93 (1H, app t, J=8.4 Hz, H-2), 3.68-3.49 (2H, m, H-3) ppm. $^{13}$C-NMR (100.6 MHz, DMSO) δ 178.1 (C-1), 163.2 (C-4), 160.5 (C-5), 146.6 (C-6), 144.1 (C-11), 135.9 (C-9), 124.2 (C-7), 114.5 (C-10), 103.9 (C-8), 81.8 (C-2), 34.5 (C-3) ppm. HRMS (ESI+): m/z Calculated for C$_{11}$H$_9$N$_3$O$_2$S$_2$ [M+K] 317.9768, found 317.9768.
D-thioluciferin Synthesis of 3-((4-aminophenyl)thio)acrylic acid

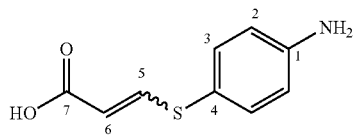

Propiolic acid (60.0 mg, 0.810 mmol, 1.05 eq) and p-aminothiophenol (100 mg, 0.800 mmol, 1 eq) were stirred in anhydrous DMF (1 mL) at room temperature under a nitrogen atmosphere for 24 h. The resulting red-brown solution was diluted with EtOAc (10 mL), washed with brine (4×10 mL), dried over MgSO$_4$ and then reduced in vacuo. The crude material was then further purified by silica column chromatography 3:7 EtOAc:Pet. ether to afford the title compound, a pale yellow solid, as a 1:9 mixture of E:Z isomers (47.0 mg, 30% yield). Mp: 113-207° C. E-isomer; $^1$H-NMR (400 MHz, CDCl$_3$) δ 12.0 (1H, br s, —COOH), 7.67 (1H, d, J=14.8 Hz, H-6), 7.14 (2H, d, J=8.5 Hz, H-3), 6.65 (2H, d, J=8.5 Hz, H-2), 5.95-5.39 (2H, br s, —NH$_2$), 5.26 (1H, d, J=14.8 Hz, H-5). $^{13}$C-NMR (100.6 MHz, CDCl$_3$) δ 166.1 (C-7), 150.1 (C-5), 149.6 (C-1), 135.8 (C-4), 115.3 (C-6), 114.8 (C-3), 112.2 (C-2) ppm. Z-isomer; $^1$H-NMR (400 MHz, CDCl$_3$) δ 12.0 (1H, br s, —COOH), 7.67 (1H, d, J=14.8 Hz, H-6), 7.14 (2H, d, J=8.5 Hz, H-3), 6.65 (2H, d, J=8.5 Hz, H-2), 5.95-5.39 (2H, br s, —NH$_2$), 5.26 (1H, d, J=14.8 Hz, H-5). $^{13}$C-NMR (100.6 MHz, CDCl$_3$) δ 167.5 (C-7), 153.0 (C-5), 149.9 (C-1), 133.3 (C-4), 120.0 (C-6) 114.9 (C-3), 113.0 (C-2) ppm.

Synthesis of 3-((4-(((Z)-4-chloro-5H-1,2,3-dithiazol-5-ylidene)amino)phenyl)thio)acrylic acid

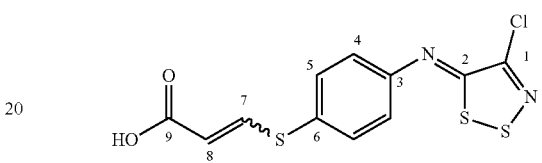

Appel's salt (0.170 g, 0.850 mmol, 1.5 eq) and a 2:8 E:Z mixture of 3-((4-aminophenyl)thio)acrylic acid (0.110 g, 0.560 mmol, 1 eq) were suspended in DCM (4 mL). The resulting suspension was stirred at room temperature under a nitrogen atmosphere for 1 h. Thereafter, anhydrous pyridine (0.09 mL, 1.12 mmol, 2 eq) was slowly added to the suspension, and the resulting mixture was allowed to stir for an additional 2 h. The reaction mixture was then concentrated in vacuo and purified by column chromatography, eluting with 3:7 EtOAc:Pet. ether to afford the title compound as a yellow solid with the ratio of geometric isomers conserved (185 mg, 99% yield). Mp: 199-201° C. E-isomer; $^1$H-NMR (400 MHz, CDCl$_3$) δ 12.36 (1H, br s, —COOH), 7.77 (1H, d, J=15.1 Hz, H-8), 7.65 (2H, d, J=8.6 Hz, H-5), 7.40-7.14 (2H, m, H-4), 5.59 (1H, d, J=15.0 Hz, H-7). $^{13}$C-NMR (100.6 MHz, CDCl$_3$) δ 165.92 (C-9), 161.13 (C-1), 152.26 (C-2), 150.98 (C-7), 147.20 (C-6), 134.83 (C-3), 133.42 (C-8), 127.37 (C-5), 121.42 (C-4) ppm. Z-isomer; $^1$H NMR (400 MHz, CDCl$_3$) δ 12.36 (1H, br s, —COOH), 7.65 (2H, d, J=8.6 Hz, H-5), 7.54 (1H, d, J=10.0 Hz, H-8), 7.40-7.14 (2H, m, H-4), 5.95 (1H, d, J=9.9 Hz, H-7). $^{13}$C-NMR (100.6 MHz, CDCl$_3$) δ 167.59 (C-9), 160.5 (C-1), 148.62 (C-7), 147.3 (C-2), 146.3 (C-3), 132.1 (C-6), 121.06 (C-8), 117.0 (C-5), 114.47 (C-4) ppm. MS (ESI+): m/z Calculated for C$_{11}$H$_7$ClN$_2$O$_2$S$_3$ [M+H] 330.9436, found 330.9430.

Synthesis of Benzyl Propiolate

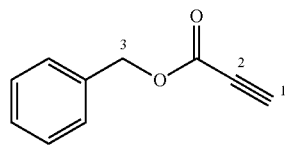

Cesium carbonate (1.1 eq) was stirred in DMF and cooled to 0° C. Propiolic acid (1.1 eq) was added dropwise to the cooled suspension. The resulting solution was left to stir for a further 20 min, maintained at 0° C., after which BnBr (1 eq) was added. After the addition, the reaction was allowed to warm to rt. The reaction mixture was then diluted with EtOAc and washed with a saturated solution of brine. The organic layer was then dried over MgSO$_4$, reduced in vacuo to afford pure benzyl propiolate in good yield. $^1$H NMR (400 MHz, CDCl$_3$) δ 7.40 (1H, m, -Ph), 5.23 (2H, S, H-3), 4.60 (1H, s, H-1).

3-((4-(((Cyanocarbonothioyl)amino)phenyl)thio)acrylic acid

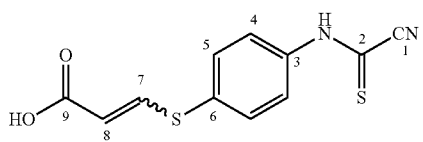 [SMILES: N#CC(=S)Nc1ccc(SC=CC(=O)O)cc1]

Method A: DBU (0.3 mL, 1.80 mmol, 3 eq) was added dropwise to a 5° C. solution of 3-((4-(((Z)-4-chloro-5H-1,2,3-dithiazol-5-ylidene)amino)phenyl)thio)acrylic acid (200 mg, 0.600 mmol, 1 eq) in freshly distilled DCM (5 mL) under a nitrogen atmosphere. The resulting red-brown mixture was stirred at 5° C. for 30 min, after which it was allowed to warm to room temperature and left to stir for a further 30 min. The reaction mixture was then washed with saturated ammonium chloride solution (2×2 mL), and H$_2$O (1×2 mL). The organic phase was dried over Na$_2$SO$_4$ and concentrated in vacuo. The crude material was purified by silica gel chromatography, eluting with 1:8.9:0.1 MeOH:EtOAc:TFA to provide the title compound as an orange oil (8.00 mg, <5% yield).

Method B: DBU (0.3 mL, 1.80 mmol, 3 eq) was added dropwise, over 30 min, to a solution of 3-((4-((cyanocarbonothioyl)-amino)phenyl)thio)acrylic acid (0.200 g, 0.600 mmol, 1 eq) in DMSO (2 mL) at room temperature under a nitrogen atmosphere. The resulting mixture was stirred for 30 min, after which it was allowed to warm to room temperature and left to stir for a further 30 min. The reaction mixture was then diluted with saturated NH$_4$Cl$_{aq}$ solution (6 mL), and washed with DCM (4×2 mL). The aqueous was concentrated under reduced pressure, MeOH (3 mL) was added and the resulting precipitate filtered under vacuum. The filtrate was then reduced in vacuo and diluted with additional MeOH (5 mL) resulting in the precipitation of trace NH$_4$Cl salts. The precipitate was filtered and the filtrate reduced and lyophilised to afford the crude product. The crude material was purified by silica gel chromatography, eluting with 1:8.9:0.1 MeOH:EtOAc:TFA to provide the title compound, in a 2:8 mixture of E:Z isomers, as a red-orange oil (52.0 mg, 33% yield). E-isomer; $^1$H-NMR (400 MHz, DMSO) δ 12.38 (1H, br s, —COOH), 9.91 (1H, br s, —NH), 7.42 (1H, d, J=15.0 Hz, H-8), 7.59 (2H, d, J=8.6 Hz, H-5), 7.11 (2H, d, J=8.6 Hz, H-4), 5.50 (1H, d, J=15.0 Hz, H-7). Z-isomer; $^1$H NMR (400 MHz, DMSO) δ 12.38 (1H, br s, —COOH), 9.91 (1H, br s, —NH), 7.65 (2H, d, J=8.6 Hz, H-5), 7.56 (1H, d, J=10.0 Hz, H-8), 7.40 (2H, m, H-4), 4.67 (1H, d, J=10.0 Hz, H-7).

Synthesis of benzyl (E)-3-((4-aminophenyl)thio)acrylate

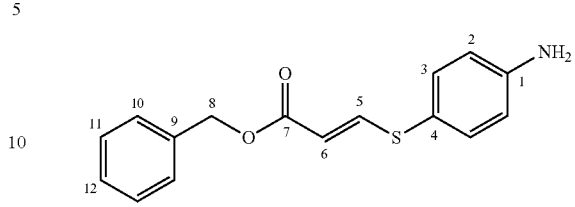

Benzyl propiolate (0.580 g, 3.63 mmol, 1 eq) and p-aminothiophenol (0.450 g, 3.63 mmol, 1 eq) were stirred in anhydrous DMF (2 mL) at room temperature under a nitrogen atmosphere for 24 h. The resulting red-brown solution was diluted with EtOAc (12 mL), washed with brine (4×6 mL), dried over MgSO$_4$ and excess solvent reduced in vacuo. The crude residue was then subjected to column chromatography eluting with 3:10 EtOAc:Pet. ether and the material obtained was recrystallised to a constant melting point from boiling pet. ether to afford the geometrically pure product as a brown solid (0.276 g, 39%). Mp: 118-119° C. $^1$H-NMR (300 MHz, CDCl$_3$) δ 7.36 (5H, m, H-10-12), 7.32 (1H, d, J=10.1 Hz, H-6), 7.14 (2H, d, J=8.5 Hz, H-3), 6.60 (2H, d, J=8.5 Hz, H-2), 5.89 (1H, d, J=10.1 Hz, H-5), 5.47 (2H, br s, —NH$_2$), 5.13 (2H, s, H-8) ppm. $^{13}$C-NMR (100.6 MHz, CDCl$_3$) δ 165.8 (C-7), 154.6 (C-6), 149.9 (C-1), 136.8 (C-5), 133.4 (C-3), 128.9 (C-10), 128.5 (C-11), 128.4 (C-12), 119.4 (C-9), 115.0 (C-2), 111.5 (C-5), 65.6 (C-8) ppm. MS (ESI+): m/z Calculated for C$_{16}$H$_{15}$NO$_2$S [M+H] 286.0901, found 286.0889.

Synthesis of benzyl (E)-3-((4-(((Z)-4-chloro-5H-1,2,3-dithiazol-5-ylidene)amino)phenyl)thio)acrylate

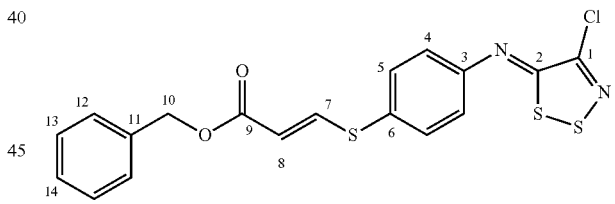

Appel's salt (0.220 g, 1.08 mmol, 2 eq) and benzyl (E)-3-((4-aminophenyl)thio)acrylate (0.150 g, 0.540 mmol, 1 eq) were dissolved in DMF (4 mL). The resulting solution was stirred at room temperature under a nitrogen atmosphere for 1 h. Thereafter, anhydrous pyridine (0.05 mL, 1.08 mmol, 2 eq) was slowly added to the solution, after which it was left to stir for an additional 2 h. The mixture was then concentrated in vacuo and purified by silica column chromatography, eluting with 1:9 EtOAc:Pet. ether, to afford the title compound as a bright yellow solid (0.225 g, 99%). Mp: 130-152 C. $^1$H-NMR (300 MHz, DMSO) δ 7.66 (3H, m, H-8.5), 7.41 (5H, m, H-12,13,14), 7.28 (2H, d, J=8.5 Hz, H-4), 6.07 (1H, d, J=10.0 Hz, H-7), 5.20 (2H, s, H-10). $^{13}$C-NMR (100.6 MHz, DMSO) δ 165.8 (C-9), 160.6 (C-2), 151.2 (C-1), 150.3 (C-7), 147.2 (C-3), 136.6 (C-6), 132.7 (C-11), 132.3 (C-5), 128.9 (C-13), 128.6 (C-14), 128.5 (C-12), 121.1 (C-4), 113.4 (C-8), 65.9 (C-10). MS (ESI+): m/z Calculated for C$_{18}$H$_{13}$ClN$_2$O$_2$S$_3$ [M+H] 420.9905, found 420.9899.

Synthesis of benzyl (E)-3-((4-((cyanocarbonothioyl)amino)phenyl)thio)acrylate

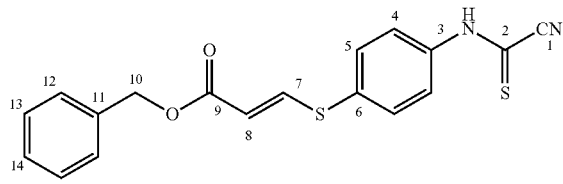 [SMILES: N#CC(=S)Nc1ccc(S/C=C/C(=O)OCc2ccccc2)cc1]

DBU (0.13 mL, 0.854 mmol, 3 eq) was added, dropwise over 30 min, to a solution of (E)-3-((4-(((Z)-4-chloro-5H-1,2,3-dithiazol-5-ylidene)amino)phenyl)thio)acrylate (0.120 g, 0.285 mol, 1 eq) in anhydrous DMSO (2 mL) at room temperature under a nitrogen atmosphere. The resulting red-brown mixture was stirred for 40 min, after which it was diluted with EtOAc (12 mL). The reaction mixture was then washed with a saturated $NH_4Cl_{aq}$ solution (3×6 mL) and $H_2O$ (1×10 mL). The organic phase was dried over $Na_2SO_4$ and concentrated in vacuo. The crude material was purified by silica gel column chromatography, eluting with 2:8 EtOAc:Hexane, to provide the title compound as a red solid (48.0 mg, 61%). Mp: 96-97 C. $^1$H-NMR (400 MHz, DMSO) δ 13.56 (1H, br s, —NH), 7.98 (2H, d, J=8.9 Hz, H-5), 7.67 (3H, app dd, J=9.5, 7.7 Hz, H-8,4), 7.41 (5H, m, H-12,13,14), 6.10 (1H, d, J=10.0 Hz, H-7), 5.20 (2H, s, H-10). $^{13}$C-NMR (100.6 MHz, DMSO) δ 165.8 (C-9), 161.8 (C-2), 149.2 (C-7), 137.9 (C-3), 136.6 (C-6), 134.7 (C-11), 130.9 (C-5), 131.3 (C-12), 128.6 (C-13), 128.5 (C-14), 123.8 (C-4), 114.2 (C-1), 113.9 (C-8), 66.0 (C-10). MS (ESI+): m/z Calculated for $C_{18}H_{14}N_2O_2S_2$ [M+H] 355.0574, found 355.0580.

Synthesis of benzyl (E)-3-((2-cyanobenzo[d]thiazol-6-yl)thio)acrylate

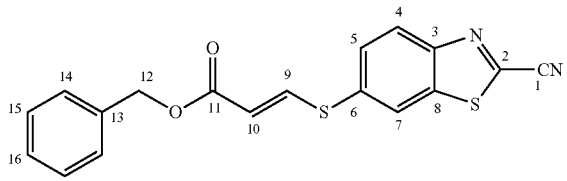 [SMILES: N#Cc1nc2ccc(S/C=C/C(=O)OCc3ccccc3)cc2s1]

Palladium chloride (4.00 mg, 0.020 mmol, 0.1 eq), copper iodide (19.0 mg, 0.099 mmol, 0.5 eq), TBAB (0.127 g, 0.394 mmol, 2 eq) and (E)-3-((4-(((Z)-4-chloro-5H-1,2,3-dithiazol-5-ylidene)amino)-phenyl)thio)acrylate (70.0 mg, 0.197 mmol, 1 eq) were suspended in anhydrous DMSO (1 mL). The resultant orange-red mixture was placed under a nitrogen atmosphere and stirred at 120° C. for 4 h. The reaction mixture was then diluted with EtOAc (6 mL) and washed with a saturated brine solution (4×2 mL). The organic layer was then dried over $Na_2SO_4$, filtered, and concentrated in vacuo. The crude product was purified by column chromatography 3:7 EtOAc:Hexane to provide the 2-cyanobenzothiazole as a yellow solid (0.0430 g, 62%). Mp: 113-120 C. $^1$H-NMR (400 MHz, DMSO) δ 8.59 (1H, d, J=1.9 Hz, H-7), 8.29 (1H, d, J=8.7 Hz, H-4), 7.85 (1H, dd, J=8.7, 1.9 Hz, H-5), 7.78 (1H, d, J=10.0 Hz, H-10), 7.41 (5H, m, H-14,15,16), 6.17 (1H, d, J=10.0 Hz, H-9), 5.22 (2H, s, H-12). $^{13}$C-NMR (100.6 MHz, DMSO) δ 165.9 (C-11), 151.4 (C-2), 148.6 (C-9), 138.4 (C-3), 137.0 (C-8), 136.8 (C-6), 136.5 (C-13), 130.1 (C-7), 128.9 (C-14), 128.6 (C-15), 128.6 (C-16), 125.6 (C-5), 124.3 (C-4), 114.5 (C-10), 113.7 (C-1), 66.1 (C-12). MS (ESI+): m/z Calculated for $C_{18}H_{12}N_2O_2S_2$ [M+H] 353.0418, found 353.0542.

Synthesis of (S,E)-2-(6-((3-(benzyloxy)-3-oxoprop-1-en-1-yl)thio)benzo[d]thiazol-2-yl)-4,5-dihydrothiazole-4-carboxylic acid

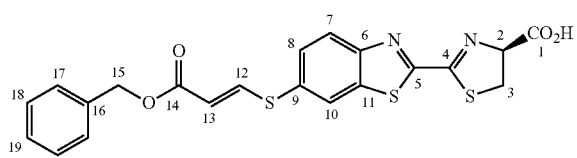 [SMILES: O=C(/C=C/Sc1ccc2nc(C3=N[C@@H](C(=O)O)CS3)sc2c1)OCc1ccccc1]

To a stirring solution of benzyl (E)-3-((2-cyanobenzo[d]thiazol-6-yl)thio)acrylate (4.00 mg, 0.0110 mmol, 1 eq) in DMSO (0.4 mL) at room temperature under a nitrogen atmosphere was added D-Cysteine (2.00 mg, 0.0110 mmol, 1 eq) in $H_2O$ (0.6 mL). The solution was left to stir for 5 min, cooled to 0 C, and then potassium carbonate (15.0 mg, 0.0110, 1 eq) was added. The reaction mixture was then left to stir a further 10 min after which the pH was adjusted to pH 3 using 3 M HCl, all whilst maintaining a reaction temperature of 0° C. The solution was then allowed to warm to room temperature and diluted with EtOAc (2 mL) and washed with $H_2O$ (4×1 mL). The organic layer was then dried over $MgSO_4$, filtered and evaporated under reduced pressure at 35° C. to afford a red oil. The crude material was further purified using silica column chromatography, eluting with 1:9 MeOH:DCM to afford the title compound as a red oil (5.00 mg, 99%). $^1$H-NMR (300 MHz, DMSO) δ 8.47 (1H, d, J=1.9 Hz, H-10), 8.20 (1H, d, J=8.6 Hz, H-7), 7.76 (2H, m, H-8,13), 7.40 (5H, m, H-19,18,17), 6.13 (1H, d, J=10.1 Hz, H-12), 5.47 (1H, dd, J=9.7, 8.5 Hz, H-2), 5.22 (2H, s, H-15), 3.77 (2H, m, H-3). MS (ESI+): m/z Calculated for $C_{21}H_{16}N_2O_4S_3$ [M+H] 457.0350, found 457.0341.

Synthesis of (S)-2-(6-mercaptobenzo[d]thiazol-2-yl)-4,5-dihydrothiazole-4-carboxylic acid

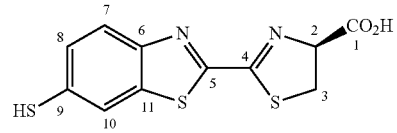

D-Cysteine hydrochloride monohydrate (15.0 mg, 0.0790 mmol, 2.01 eq) and benzyl (E)-3-((2-cyanobenzo[d]thiazol-6-yl)thio)acrylate (14.0 mg, 0.0397 mmol, 1 eq) were suspended in DMSO (0.4 mL) at room temperature under a nitrogen atmosphere. Potassium carbonate (35.0 mg, 0.119 mmol, 3 eq) dissolved in water (0.4 mL) was then added to the mixture, and the resulting bright orange solution was stirred under an inert atmosphere for a further 10 min. Upon consumption of benzyl (E)-3-((2-cyanobenzo[d]thiazol-6-yl)thio)acrylate, as evidenced by TLC analysis, the methanol was removed in vacuo and the remaining aqueous solution acidified to pH 3 with 3 M HCl. The aqueous was then extracted with EtOAc (5×1 mL). The combined organics were dried over $NaSO_4$, filtered, concentrated in vacuo and purified with column chromatography 1:8.9:0.1 MeOH:DCM:TFA to provide D-thioluciferin as a pale yellow solid (11.0 mg, 99%). [α]20/D obs: −11°, DMF, c=1. Mp: 89-90° C. $^1$H-NMR (400 MHz, DMSO) δ 8.49 (1H, s, H-10), 8.18 (1H, dd, J=8.7, 0.5 Hz, H-7), 7.78 (1H, dd, J=8.7, 2.0 Hz, H-8), 5.45 (1H, dd, J=9.8, 8.3 Hz, H-2), 3.75 (2H, m, H-3) ppm. $^{13}$C-NMR (100.6 MHz, DMSO δ 177.5 (C-1), 166.3 (C-4), 163.2 (C-11), 155.4 (C-5), 150.5 (C-6), 130.0 (C-9), 125.5 (C-7), 123.0 (C-10), 121.9 (C-8), 82.1 (C-2), 34.5 (C-3) ppm. HRMS (ESI+): m/z Calculated for $C_{11}H_8N_2O_2S_3$ [M+Na] 318.9645, found 319.0000.

Luminescence and Fluorescence Evaluation
Purified Protein Luminescence Assays

Luminescence assays were initiated by adding 30 μL of purified luciferase in enzyme buffer (20 mM Tris [pH 7.4], 0.1 mM EDTA, 1 mM TCEP, and 0.8 mg/mL BSA) to 30 μL 2× substrate in substrate buffer (20 mM Tris [pH 7.4], 0.1 mM EDTA, 8 mM MgSO4, and 4 mM ATP) in a black 96-well plate. Imaging was performed one minute after enzyme addition using a Xenogen® IVIS-100® at a final enzyme concentration of 10 nM and final substrate concentrations ranging from 0.122 to 250 μM. Data acquisition and analysis was performed with Living Image® software. Data are reported as total flux (p/s) for each ROI corresponding to each well of the 96-well plate.

Bioluminescence Emission Scans

Purified luciferase in enzyme buffer was rapidly injected into a cuvette containing substrate in substrate buffer to a final enzyme concentration of 100 nM and a final substrate concentration of 10 μM. The emission from 400 to 800 nm was recorded in a fluorimeter with closed excitation slits 10 s after injection.

Burst Kinetics Assays

Using a Turner Biosystems 20/20n luminometer, 40 μL of purified luciferase in enzyme injection buffer (20 mM Tris [pH 7.4], 0.1 mM EDTA, 0.625 mM TCEP, and 0.5 mg/mL BSA) was rapidly injected into a clear microcentrifuge tube containing 10 μL of substrate in substrate injection buffer (20 mM Tris [pH 7.4], 0.1 mM EDTA, 20 mM MgSO4, and 10 mM ATP) to a final enzyme concentration of 0.2 nM and a final luciferin substrate concentration of 250 μM. Measurements were taken every 0.2 s for 1 s pre-injection and 120 s post-injection. Data acquisition was performed with SIS for 2020n v1.9.0 software. Data are reported as Relative Light Units (RLU). To correct for the wavelength sensitivity of the PMT in the 20/20n, total flux was also measured using the IVIS-100 as described above with a final enzyme concentration of 10 nM and a final substrate concentration of 250 μM. Data from the IVIS and from the 20/20n at the 60 s time point were normalised to the WT+D-luciferin value. The correction factor of each enzyme/substrate pair was calculated by dividing the normalized IVIS data by the normalised 20/20n data. All 20/20n data were then multiplied by their respective correction factors.

UV-Vis Experiments (Absorption Sectra)

Absorption spectra for D-Luciferin, luciferin-analogues and all precursor 2-cyanobenzothiazoles were recorded with a Cary 60 spectrophotometer, instrument version 2.00. Samples were prepared as a 0.01 mM DMSO solution unless otherwise stated and were scanned from 200 nm to 650 nm at a UV-Vis scan rate of 24000.00 nm/min. Data were analysed using Scan Software Version 5.0.0.999.

Fluorescence Spectrophotometry (Excitation Emission Spectra)

Excitation and emission spectra were recorded on a Varian Cary Eclipse fluorometer equipped with a regulated temperature cell holder and Hellma, Suprasil® quartz fluorescence cuvettes of 10 mm pathlength and 1.5 mL volume capacity. Emission spectra were recorded at an excitation wavelength corresponding to previously recorded absorption maxima. Samples were prepared as a 0.1 mM DMSO solution, unless otherwise stated, and were scanned from 200 nm to 800 nm (Ex. Slit/Em. Slit 5 nm) at a scan rate of 600.00 nm/mn. Data were analysed using Scan Software Version 1.1.

Luminescence and Fluorescence Results

The compounds of Formula (I) were evaluated in in vitro assays to determine their binding to luciferase enzyme. The results are illustrated in the accompanying FIGS. 1 to 15 and in Table 3 and Table 4 below.

TABLE 3

Comparative luminescence data of D-thioluciferin, D-aminoluciferin and D-luciferin

|  | D-Luciferin | D-Aminoluciferin | D-Thioluciferin |
| --- | --- | --- | --- |
| $\lambda_{max}$ | 553 nm | 597 nm | 599 nm |
| $\lambda_{max}$ (lit.) | 551 nm | 594 nm | — |
| $V_{max}$ | 57 ± 13 RLU/s | 13 ± 2.2 RLU/s | 0.7597 ± 0.1071 RLU/s |
|  |  |  | 0.6661 ± 0.1522 RLU/s |
| $V_{max}$ (lit.) | 1626 ± 24 photons/min | 169 ± 2.6 photons/min | — |
|  | 1.027 ± 0.036 × 10$^{-5}$ RLU/s |  |  |
| $K_m$ (App.) | 8.3 ± 0.5 μM | 0.39 ± 0.08 μM | 0.1169 ± 0.01163 μM |
|  |  |  | 0.098 ± 0.01471 μM |
| $K_m$ (lit) | 9.15 ± 1.32 μM | 0.62 ± 0.05 μM | — |
|  | 16 ± 1 μM |  |  |
|  | 14.8 ± 1.9 μM |  |  |
|  | 7 μM |  |  |
| Fluorescence | — | — | 500 nm |
| Fluorescence (lit.) | 528 nm | 517 nm | — |

As shown in the Table 4, the results of the assays show that D-thioluciferin sustains light of constant intensity over a period of 20 minutes, whereas the native D-luciferin and the amino derivative display rapid decreases in luminescent activity, 1 minute post-addition for D-aminoluciferin and 10 minutes post-addition for D-luciferin. The measured rates of reduction in luminescence suggests that D-thioluciferin emission has a longer half-life than D-luciferin and D-aminoluciferin.

TABLE 4

Relative rates of reduction in luminescence. Rates are measured for 15 seconds post-specified times and reported in RLU/s

|  | Rate 1 min post-peak emission | Rate 5 min post-addition | Rate 20 minutes post addition |
|---|---|---|---|
| D-Luciferin | — | 9.300 ± 0.9815 | 0.3400 ± 0.05773 |
| D-Aminoluciferin | — | 1.216 ± 0.1305 | 0.1510 ± 0.007506 |
| D-thioluciferin | 4.929 ± 0.1584 | 0.006700 ± 0.003753 | 0.002200 ± 0.00000001377 |

Figure 7:
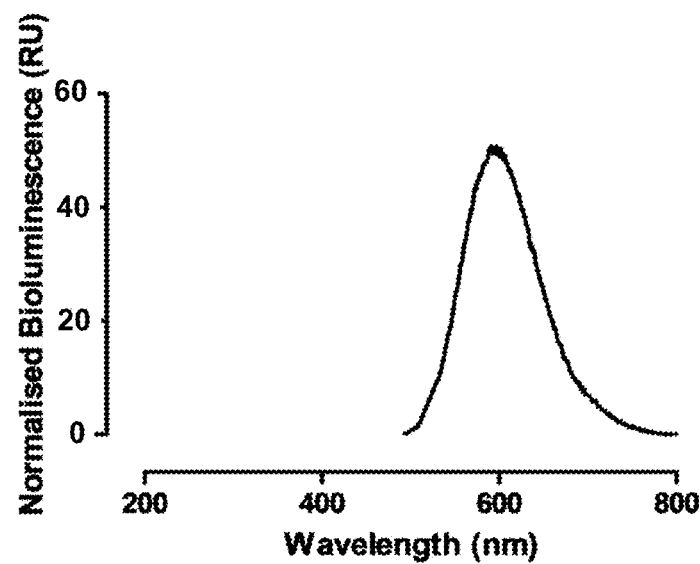
FIG. 7 is a bioluminescence emission spectrum for 10 nM luciferase with 100 μM D-thioluciferin. The spectrum shows that D-thioluciferin is a substrate for WT luciferase and demonstrates the more red-shifted wavelength of emission observed for D-thioluciferin (600 nm) relative to D-luciferin (547 nm).

FIG. 7 shows the bioluminescence emission wavelength of D-thioluciferin. It can be seen from the graph that D-thioluciferin exhibits a more red-shifted emission (599 nm) when treated with purified firefly luciferase (luc) expressed from E. coli, relative to D-Luciferin (557 nm) and D-aminoluciferin (593 nm). This longer wavelength relative to the natural substrate makes D-thioluciferin better suited for deep tissue imaging, since longer and more red-shifted emission maxima are required for tissue penetration. In addition, D-thioluciferin can be used concurrently with D-luciferin for dual imaging, since their respective maximum wavelengths of emission are sufficiently different.

Figure 8:
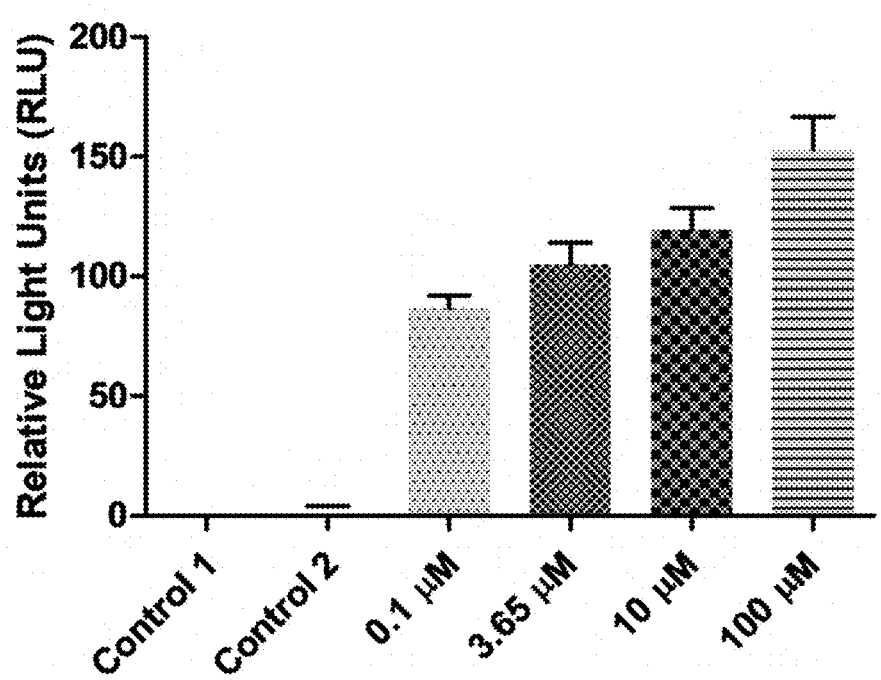
FIG. 8 is a graph of luciferase luminescence at a final enzyme concentration of 10 nM, at varying D-thioluciferin concentrations 1 min post-enzyme addition (control 1 is the emission recorded for the enzyme solution in the absence of D-thioluciferin and control 2 is the recorded emission for D-thioluciferin in the absence of the enzyme).
Figure 9:
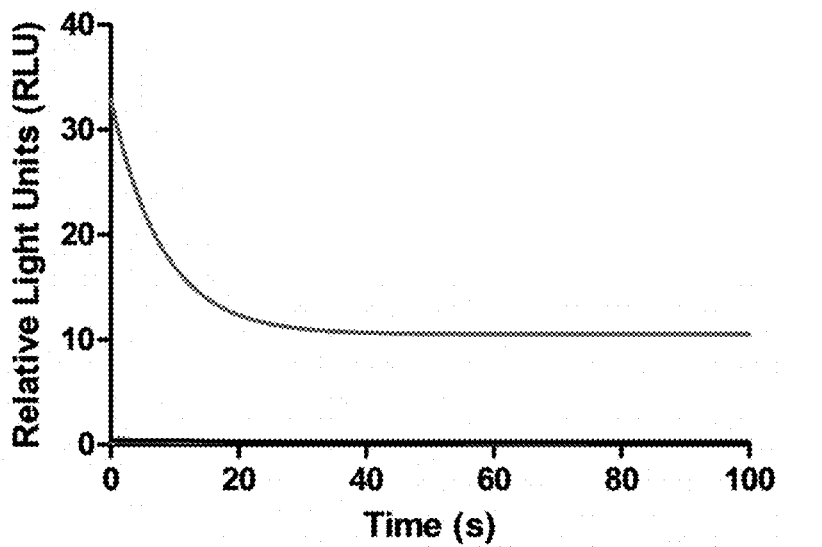
FIG. 9 is a burst kinetics profile of purified 10 nM luciferase treated with 100 µM D-thioluciferin.

FIGS. 8-13 highlight the bioluminescence properties of D-thioluciferin and its analogues. As shown in FIG. 8, no emission was observed for the pure enzyme in the absence of a luciferin (control 1) as well as for the pure substrate in the absence of enzyme (control 2). This means that any luminescence observed must be due to the reaction of D-thioluciferin with the luciferase enzyme. The burst kinetics profile of D-thioluciferin (FIG. 9) was similar to that reported for both D-luciferin and D-aminoluciferin indicating that the new thio-analogue interacts with the luciferase enzyme in a similar manner to the natural compound. The burst kinetic profile (FIG. 9) showed how D-thioluciferin gave a robust initial burst of light followed by sustained light output of much lower intensity. This trend is consistent with that previously reported for D-luciferin and D-aminoluciferin where rapid decay in emission intensity post-burst corresponds to product inhibition.

Figure 10:
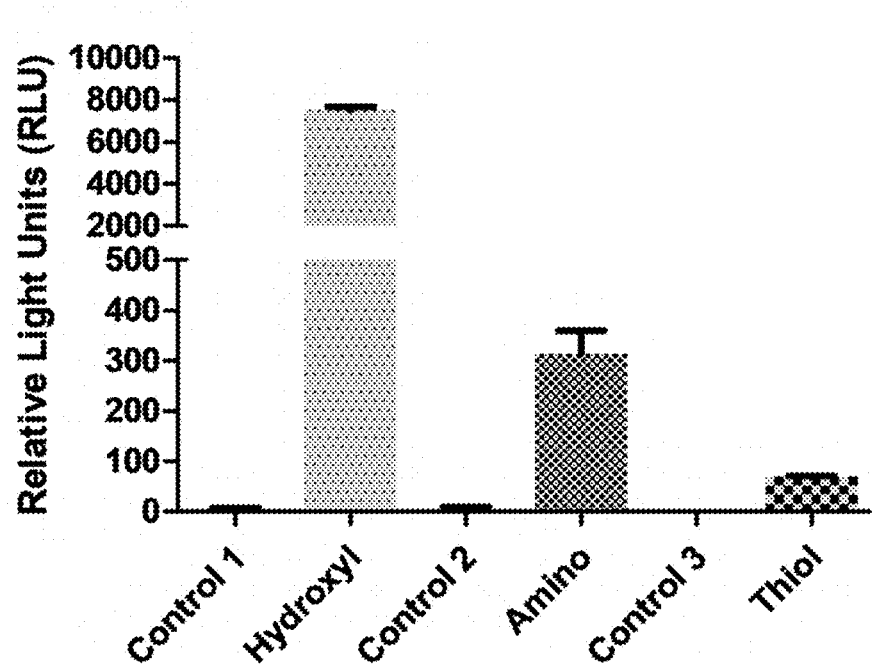
FIG. 10 is a relative luminescence emission intensity of the core luciferins (6-hydroxy, 6-amino, 6-thiol) at 0.1 µM substrate concentration and at a final luciferase concentration of 10 nM.

FIG. 10 shows comparative luminescent emission intensities for D-luciferin, D-aminoluciferin and D-thioluciferin. The relative luminescence emission intensity of natural D-luciferin (FIG. 10) was 100-fold greater than both D-aminoluciferin and D-thioluciferin when treated with purified WT luc as compared with the corresponding controls 1-3 (substrates in the absence of WT luc). As experienced with D-aminoluciferin, D-thioluciferin was also found to have a 100-fold less intense emission signal when compared to D-luciferin. The reduction in light output could be due to the D-thioluciferin/luciferase light emitting reaction having a lower quantum yield or because of differences in the rate of oxyluciferin production. The lower emission intensity of D-thioluciferin relative to the natural substrate D-luciferin should however not be a deterrent for its applications in bioluminescence imaging, since such experiments rely purely on light generated from the enzyme-substrate reaction and as a result, have generally good sensitivity (D-thioluciferin displayed >100-fold greater emission over the background).

Figure 11:
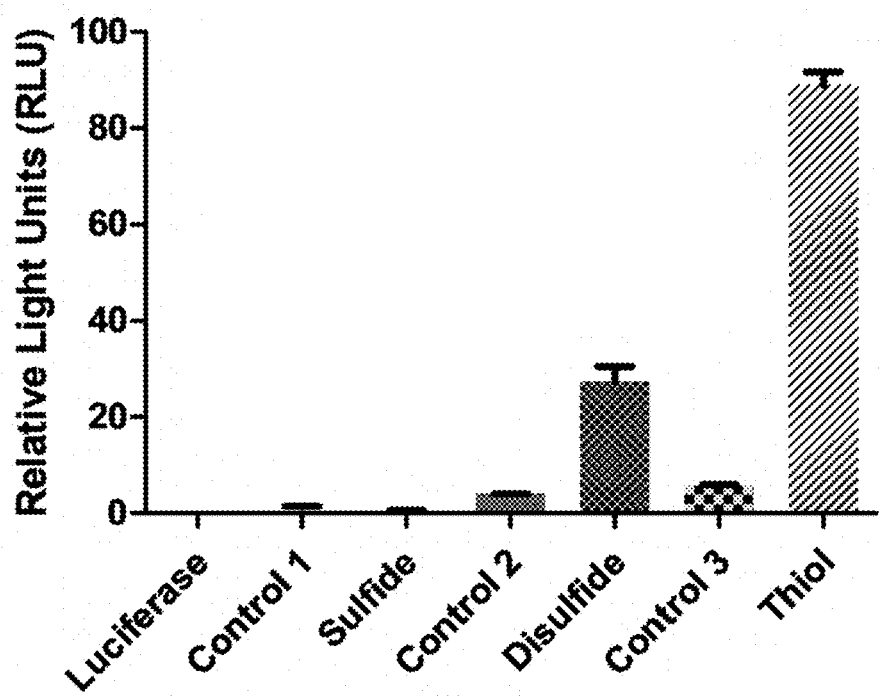
FIG. 11 illustrates luminescence output of 0.1 µM of protected D-thioluciferin sulfide, D-thioluciferin homodisulfide, and free D-thioluciferin at a final luciferase concentration of 10 nM (control readings were recorded for substrates in the absence of the luc enzyme). The RLU were determined in triplicate and are represented as the mean±SEM.
Figure 12:
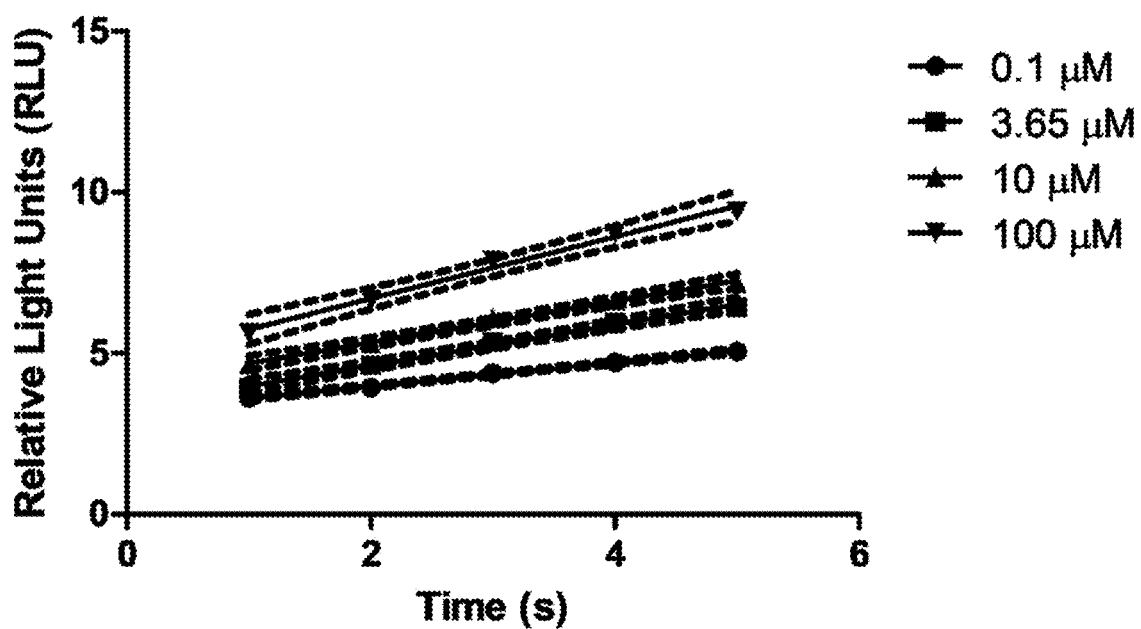
FIG. 12 shows kinetic data used to calculate the Michaelis-Menten graph of FIG. 13.

The thioacrylate sulfide and the disulfide of D-thioluciferin were also evaluated for the ability to produce bioluminescence, neither of which appeared to be bioluminescent substrates. Importantly, for the purpose of thiol sensing, the luminescence output for D-thioluciferin was 90-fold greater than its protected thioacrylate (i.e sulfide) and 2.5-fold greater than the homo-disulfide when treated with luc under physiological conditions (FIG. 11). It was demonstrated that neither pure luciferase nor pure D-thioluciferin thioacrylate (control 1) emitted light. It was also demonstrated that when a 0.1 µM thioacrylate solution was treated with luciferase in enzyme buffer, the luminescence output remained negligible. This reinforces that the thioacrylate of D-thioluciferin is indeed not a substrate for luciferase mediate bioluminescence and perhaps by extension that all sulfides of D-thioluciferin are inactive, as is the case with D-luciferin and its 6'-O-alkyl analogues. In FIG. 11, controls 2-3 contained D-thioluciferin disulfide and D-thioluciferin, respectively. In both cases, in the absence of luciferase, a small degree of luminescence was detected. The luminescence increased significantly when D-thioluciferin and its disulfide were treated with luciferase to a final enzyme concentration of 10 nM. Notably, the homodisulfide treated with luciferase had a much higher luminescence output than its corresponding control when compared to the sulfide and its corresponding control, since both were predicted to be inactive as bioluminescence substrates. This was most likely due to the reduction of the bioluminescence inactive D-thioluciferin disulfide to the bioluminescence active free thiol by reducing agents in the enzyme buffer, namely DTT. The free thiol displayed five-fold greater luminescence than the disulfide.

Figure 13:
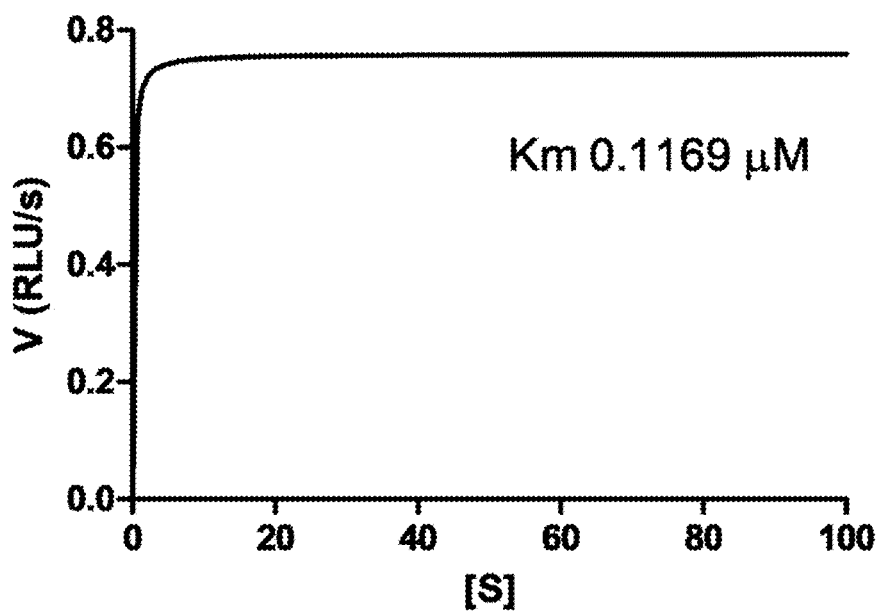
FIG. 13 is a Michaelis-Menten graph for D-Thioluciferin. The data indicates that D-thioluciferin is a relatively good substrate for the WT luc enzyme, displaying a better enzyme binding affinity when compared to natural D-luciferin ($K_m$ of 0.1 µM relative 8 µM for D-luciferin), albeit with a decreased emission intensity. The assays were performed in triplicate and are represented as the mean and each curve was fit to the Michaelis-Menten equation by nonlinear regression (GraphPad 5.0) to determine apparent $K_m$ and $V_{max}$.

Using a plot of initial rates (FIG. 12), the apparent $K_m$ of D-thioluciferin, and as reference, the $K_m$'s for D-luciferin and D-aminoluciferin were calculated using the Michaelis-Menten equation (see FIG. 13). As predicted, D-thioluciferin displayed the expected increase in the rate of emission with increasing concentration. The apparent $K_m$ was then calculated as 0.1169 µM, which was in the same order as that previously calculated for D-aminoluciferin (0.39-0.69 µM) and related analogues. The $K_m$ was surprisingly much lower than that of the native substrate, D-luciferin (8.3 µM), despite the lower emission intensity at the same concentration. The latter result along with the fact that the D-thioluciferin/luciferase light emitting reaction has a relatively lower quantum yield compared to D-luciferin, sheds some light on the bioluminescence activity of D-thioluciferin.

Figure 14:
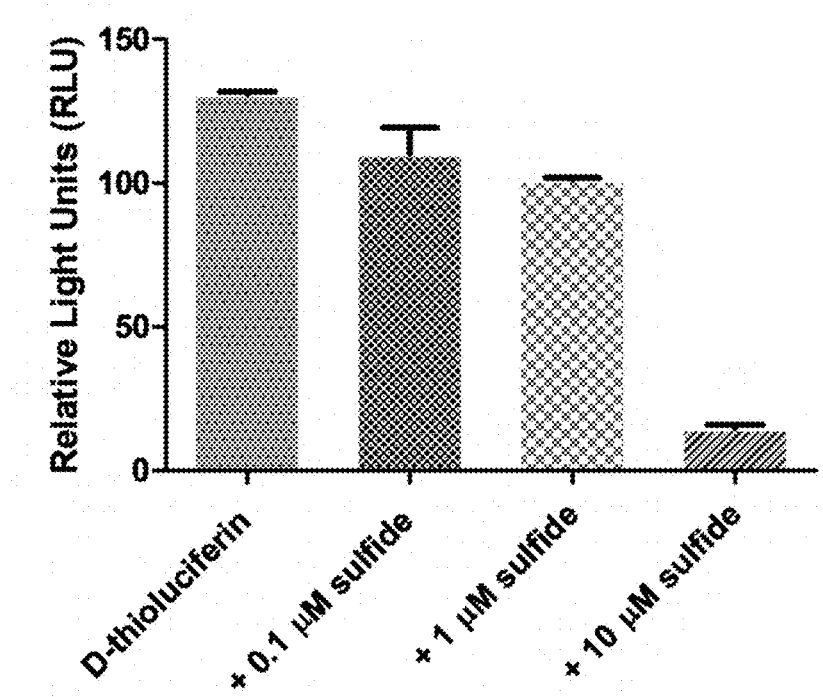
FIG. 14 is a bar graph showing potential inhibitory effects of firefly luciferase by D-thioluciferin sulfide (thioacrylate). D-thioluciferin (10 µM) was treated with purified firefly luciferase (10 nM) expressed from *E. coli* and the luminescence recorded in the absence and presence of the sulifide. The graph demonstrates a decrease in emission intensity with increasing concentration of the sulfide.
Figure 15:
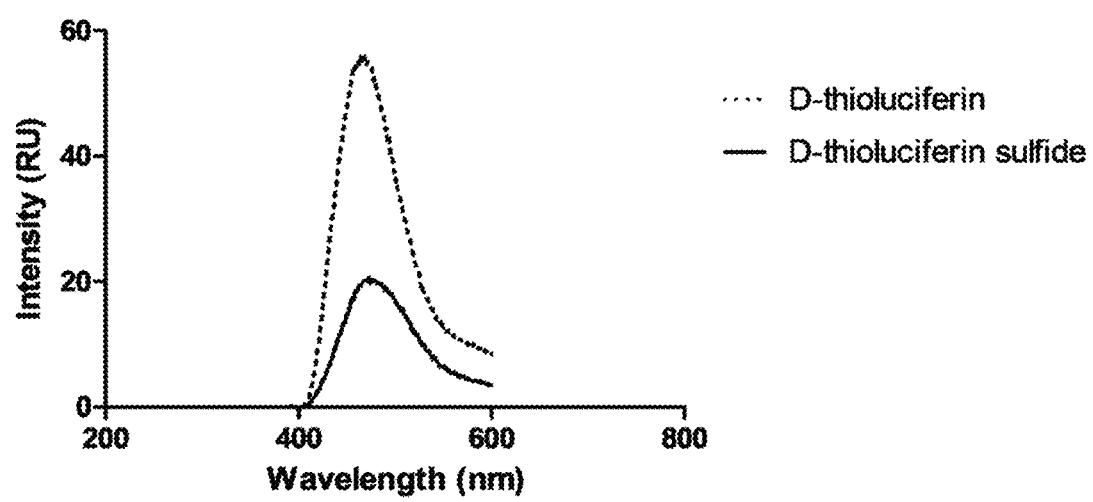
FIG. 15 shows the fluorescence emission spectra of D-thioluciferin and D-thioluciferin thioacrylate resulting from excitation at 390 nm. The free D-thioluciferin has a greater intensity relative to the sulfide which is promising for further sensor development.

Since only the thiol was predicted to be bioluminescent, the sulfide was evaluated as an inhibitor of luciferase where it was shown to be strongly inhibitory (FIG. 14). The sulfide's inhibition of luciferase could similarly be used to inform the design of D-thioluciferin based probes where disulfides inhibition is relieved upon introduction of a reductant. These types of chemistries can only be accessed by D-thioluciferin via its thio-handle.

In addition to its bioluminescent emission, D-thioluciferin was found to have a strong fluorescence emission while its protected sulfide was only weakly fluorescent (FIG. 15), thus providing further opportunities for imaging applications.

The invention claimed is:

1. A compound having the structure of Formula (I):

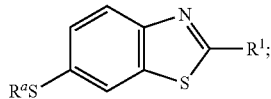

Formula (I)

wherein:

R¹ is CN or

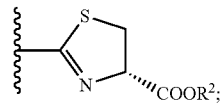

R² is H;

Rᵃ is H, halogen, optionally substituted cycloalkyl, optionally substituted heterocyclyl,

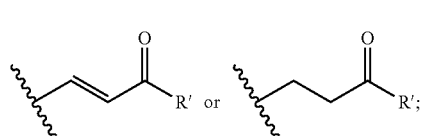

R' is H or OR"; and

R" is H;

or a salt, hydrate or solvate thereof.

2. A compound as claimed in claim 1, wherein Rᵃ is H or halogen.

3. A compound as claimed in claim 1, which is selected from the group consisting of:

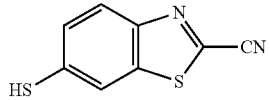

1-1

1-2

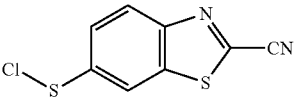

1-3

1-4

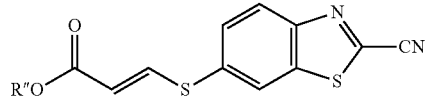

1-7

1-8

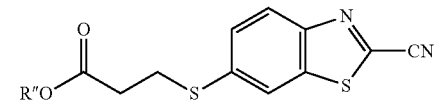

1-9

-continued 1-10

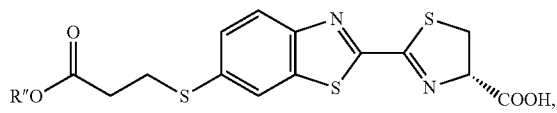

or a salt, hydrate or solvate thereof.

4. A compound as claimed in claim 3, which is

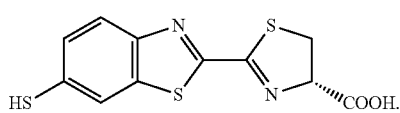

5. A probe for a luminescence assay, the probe comprising a compound as claimed in claim 1.

6. A probe as claimed in claim 5, wherein the compound has a structure selected from:

1-1

1-2

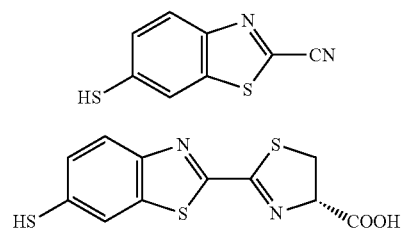

1-3

1-4

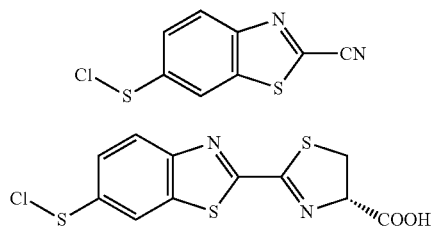

1-7

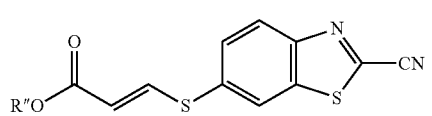

1-8

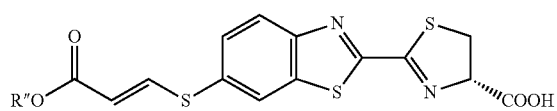

1-9

1-10

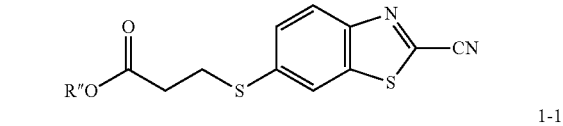

1-12

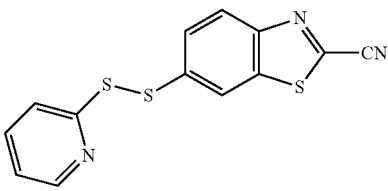

1-13

1-14

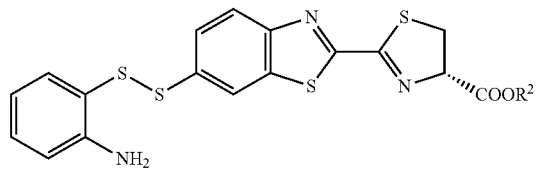

1-15

1-16

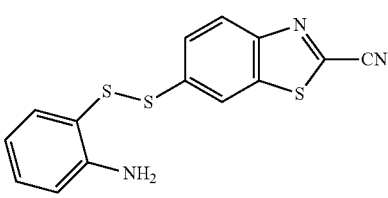

or a salt, hydrate or solvate thereof.

7. A luciferase substrate comprising a compound as claimed in claim 1.

8. A kit for a luminescence assay, the kit comprising a compound as claimed in claim 1 and optionally one or more components selected from the group consisting of a luciferase enzyme having an amino acid sequence that has at least 80% sequence identity with SEQ ID NO: 1 or with any subsequence thereof, ATP, coenzyme A and $Mg^{2+}$.

9. A method of biological imaging, the method comprising contacting, or causing to be contacted, a compound as claimed in claim 1 with a luciferase enzyme having an amino acid sequence that has at least 80% sequence identity with SEQ ID NO: 1 or with any subsequence thereof in a subject or biological sample, and detecting a fluorescence or luminescence signal resulting from the contact.

10. A method of synthesising a compound having the structure of Formula (I):

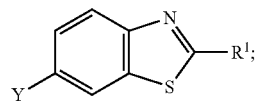

Formula (II)

wherein:

R¹ is CN or

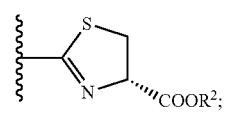

R² is H;

Rᵃ is H, halogen, optionally substituted cycloalkyl, optionally substituted heterocyclyl,

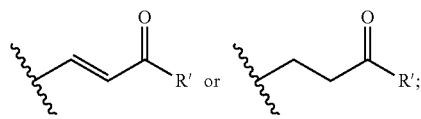

R' is H or OR''; and

R'' is H;

or a salt, hydrate or solvate thereof;

the method comprising the steps of:

(i) reacting a compound having the structure of Formula (XVI)

Formula (XVI)

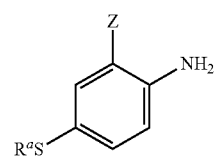

wherein Z is Cl, Br or I, with a 1,2,3-dithiazole in a suitable solvent to yield a compound having the structure of Formula (VII)

Formula (XVII)

where Hal is a halogen; and (ii) reacting the compound obtained in step (i) with a base selected from the group consisting of amidine bases, imidazole, alkali metal alkoxide bases, guanidine bases, 1,4-diazabicyclo[2.2.2]octane (DABCO), diisopropylethylamine (DIPEA), 2,6-di-tert-butylpyridine and phosphazene bases, to yield a compound having the structure of Formula (I) where R¹ is CN:

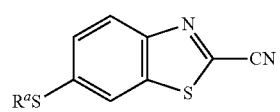

and (iii) optionally reacting the compound obtained in step (ii) with D-cysteine or an alkyl ester thereof to yield a compound of Formula (I) where R¹ is

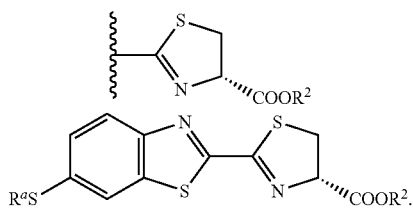

11. A method as claimed in claim 10, wherein the 1,2,3-dithiazole has the structure of Formula (VI):

Formula (VI)

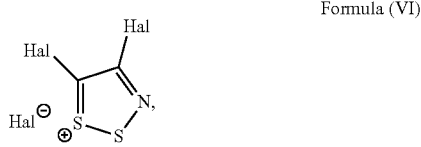

where each Hal is a halogen independently selected from Cl and Br.

12. A method as claimed in claim 10, wherein the base is 1,8-diazabicyclo[5.4.0]undec-7-ene (DBU) or 1,5-diazabicyclo[4.3.0]non-5-ene (DBN).

13. A method as claimed in claim 10, further comprising reacting a compound of Formula (XII):

Formula (XII)

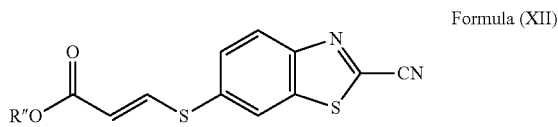

with a thiolate, alkoxide or D-cysteine to produce a compound of Formula (I) where R¹ is CN and Rᵃ is H

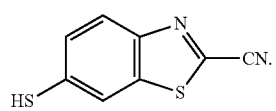 [SMILES: N#Cc1nc2ccc(S)cc2s1]

14. A method as claimed in claim 10, further comprising reacting a compound of Formula (XII)
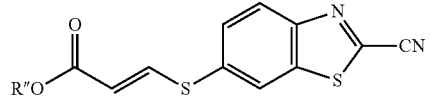
Formula (XII)
with D-cysteine to produce D-thioluciferin
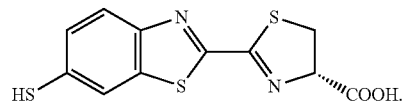 [SMILES: O=C(O)[C@H]1CSC(c2nc3ccc(S)cc3s2)=N1]
* * * * *

UNITED STATES PATENT AND TRADEMARK OFFICE
CERTIFICATE OF CORRECTION

Page 1 of 2

PATENT NO. : 11,149,034 B2
APPLICATION NO. : 16/633859
DATED : October 19, 2021
INVENTOR(S) : Moegamat Anwar Jardine et al.

It is certified that error appears in the above-identified patent and that said Letters Patent is hereby corrected as shown below:

In the Claims

At Column 46, Lines 1-45, Structures 1-12 – 1-16, delete " 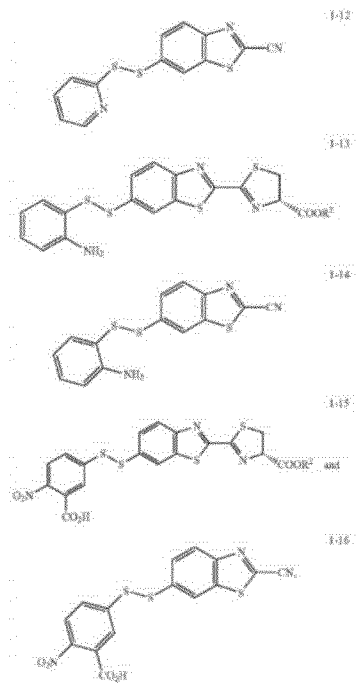 ".

At Column 47, Lines 5-10, " 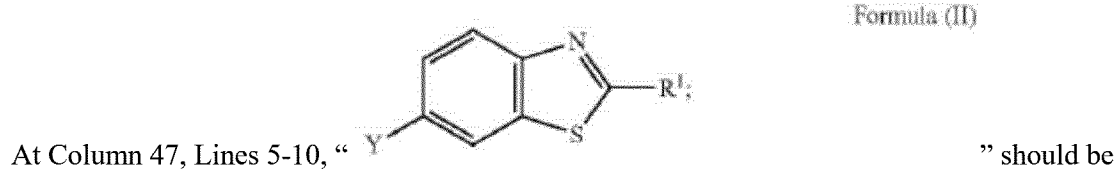 " should be

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*

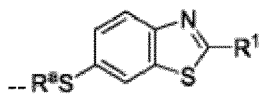
Formula (I); --.
At Column 47, Line 56, "(VII)" should be -- (XVII) --.

SEQUENCE LISTING

<160> NUMBER OF SEQ ID NOS: 1

<210> SEQ ID NO 1
<211> LENGTH: 550
<212> TYPE: PRT
<213> ORGANISM: Photinus pyralis

<400> SEQUENCE: 1

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Ser Pro Lys Gly Val
        195                 200                 205

Ala Leu Pro His Arg Thr Ala Cys Val Arg Phe Ser His Ala Arg Asp
210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
        370                 375                 380

Asn Gln Arg Gly Glu Leu Cys Val Arg Gly Pro Met Ile Met Ser Gly
385                 390                 395                 400

Tyr Val Asn Asp Pro Glu Ala Thr Asn Ala Leu Ile Asp Lys Asp Gly
```

-continued

```
                 405                 410                 415
Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Cys Gln
            435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Gly Asp Asp Ala Gly Glu Leu
465             470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
            530                 535                 540

Gly Gly Lys Ser Lys Leu
545             550
```